US008383859B2

(12) United States Patent
Thadani et al.

(10) Patent No.: US 8,383,859 B2
(45) Date of Patent: Feb. 26, 2013

(54) METHODS OF PREPARING PRIMARY, SECONDARY AND TERTIARY CARBINAMINE COMPOUNDS IN THE PRESENCE OF AMMONIA

(76) Inventors: Avinash N. Thadani, Windsor (CA); Bhartesh Dhudshia, Windsor (CA)

( * ) Notice: Subject to any disclaimer, the term of this patent is extended or adjusted under 35 U.S.C. 154(b) by 429 days.

(21) Appl. No.: 12/593,782

(22) PCT Filed: Mar. 28, 2008

(86) PCT No.: PCT/CA2008/000568
§ 371 (c)(1),
(2), (4) Date: Mar. 9, 2010

(87) PCT Pub. No.: WO2008/119162
PCT Pub. Date: Oct. 9, 2008

(65) Prior Publication Data
US 2010/0174090 A1   Jul. 8, 2010

Related U.S. Application Data

(60) Provisional application No. 60/908,994, filed on Mar. 30, 2007.

(51) Int. Cl.
*C07C 209/00* (2006.01)
(52) U.S. Cl. ......... 564/308; 564/336; 564/384; 564/471
(58) Field of Classification Search ............... None
See application file for complete search history.

(56) References Cited

U.S. PATENT DOCUMENTS

| 5,166,443 | A | 11/1992 | Merger et al. |
| 5,986,141 | A | 11/1999 | Liang |
| 6,525,222 | B2 | 2/2003 | Nouwen et al. |
| 2005/0148792 | A1 | 7/2005 | Gopal |

FOREIGN PATENT DOCUMENTS
CN  1704397 A  12/2005

OTHER PUBLICATIONS

Aydin J. et al. Journal of Organic Chemistry. 2007. 72:4689-4697.
Dhudshia, B., Tiburcio, J. and Thadani, A.N. Chem. Commun. 2005, 5551-5553.
Gross, T. et al. Organic Letters. 2002. 4(12):2055-2058.
S. Kobayashi, K. Hirano and M. Sugiura, J. Chem. Commun., 2005, 104-105.
Miriyala B., et al., Tetrahedron. 2004. 60:1463-1471.
Radionow, W.M. et al. Journal of American Chemical Society. (1929), 841-847.
M. Sugiura, K. Hirano and S. Kobayashi, J. Am. Chem. Soc., 2004, 126, 7182-7183.
M. Sugiura, C. Mori and S. Kobayashi, J. Am. Chem. Soc., 2006, 128, 11038-11039.
Solin N. et al. Organic Letters. 2005. 7(4):689-691.
Tremblay-Morin et al. Tetrahedron Letters. 2004. 45:3471-3474.
Xiang, S. et al. Fujian Shifan Daxue Xuebao, Ziran Kexueban. 1998, 14 (4):47-51. (Abstract, reaction scheme).

*Primary Examiner* — Zinna Northington Davis
(74) *Attorney, Agent, or Firm* — Bereskin & Parr LLP/S.E.N.C.R.L., s.r.l.; Michael Fenwick

(57) ABSTRACT

The present application relates to novel methods for the preparation of primary, secondary and tertiary carbinamine compounds, particularly the preparation of compounds of formulae I, IV and VI, from a carbonyl compound of formula II in the presence of ammonia or an ammonium equivalent of the formula $NH_4^+X^-$, by way of allylation, crotylation, arylation, reductive amination and catalytic hydrogenation.

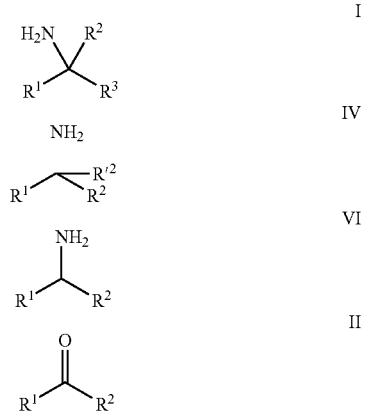

23 Claims, No Drawings

METHODS OF PREPARING PRIMARY, SECONDARY AND TERTIARY CARBINAMINE COMPOUNDS IN THE PRESENCE OF AMMONIA

This application is a national phase entry of PCT/CA2008/000568, filed Mar. 28, 2008, which claims priority from U.S. Provisional patent application Ser. No. 60/908,994 filed Mar. 30, 2007.

FIELD OF THE APPLICATION

The present application relates to methods for the preparation of carbinamine compounds, particularly the preparation of primary, secondary and tertiary carbinamine compounds, from carbonyl compounds in the presence of ammonia.

BACKGROUND OF THE APPLICATION

Amines are one of the most common classes of organic molecules. They play important roles in a variety of areas, ranging from the pharmaceutical industry to plastics manufacturing.

Current methods for the synthesis of amines generally rely on multi-step processes that convert a variety of amine precursors to the amino ($NH_2$) functional group itself. To date, with the singular exception of two existing methodologies, there has been no general method for the direct synthesis of amines from ammonia. Since ammonia is an inexpensive bulk commodity chemical that is manufactured on a multi-ton scale annually, any process that allows for the direct use of ammonia for the introduction of the amino group is therefore highly desirable.

A robust methodology for the diastereoselective allylation and crotylation of in-situ generated ketimines in the presence of ammonia has recently been developed [Dhudshia, B., Tiburcio, J. and Thadani, A. N. Chem. Commun. 2005, 5551-5553]. The resulting homoallylic amines obtained from the allyl- and crotylboronic acids addition to ketones in methanolic ammonia were reported in good to excellent yields.

SUMMARY OF THE APPLICATION

Methods for the preparation of primary, secondary and tertiary carbinamines from carbonyl compounds and nucleophiles in the presence of ammonia or an ammonia equivalent have been developed and shown to be expedient in synthesizing amines under mild reaction conditions.

Accordingly, the present application relates to a method of preparing an amine of formula I:

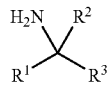

I comprising reacting a compound of formula II with a compound of formula III:

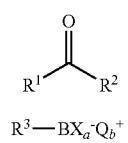

II

III in the presence of ammonia $NH_3$ or an ammonia equivalent of the formula $NH_4^+Y^-$, wherein $R^1$ is H or $C(O)R^4$ in which $R^4$ is $NR^5R^6$ or $OR^7$, and $R^2$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;

or $R^1$ and $R^2$ are independently selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;

or $R^1$ and $R^2$ are linked to form an optionally substituted monocyclic or polycyclic ring system having 4 to 20 atoms including the carbonyl to which $R^1$ and $R^2$ are bonded and one or more of the carbons of the ring system is optionally replaced with a heteromoiety selected from O, S, N, $NR^8$ and $NR^8R^9$;

$R^3$ is selected from aryl, heteroaryl,

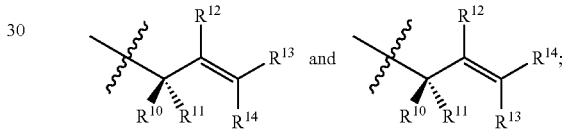

$R^{10}$ to $R^{14}$ are independently selected from H, $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, the latter 9 groups being optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;

$R^5$, $R^6$, $R^7$, $R^8$ and $R^9$ are independently selected from H, $C_{1-20}$alkyl, $C_{3-20}$cycloalkyl, aryl and heteroaryl with the latter 4 groups being optionally substituted, X is an anionic ligand;

Y is an anionic counter ion;

Q is a cationic counter ion;

a is an integer representing the number of the anionic ligands X required to fulfill the valency requirements of B and Q; and b is an integer representing the number of the cationic counter ions Q required to fulfill the valency requirements of X and B.

In another aspect, the present application relates to a method of preparing an amine of formula IV:

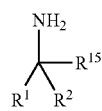

IV comprising reacting a compound of formula II with a compound of formula V:

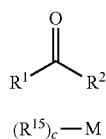

in the presence of ammonia $NH_3$ or an ammonia equivalent of the formula $NH_4^+Y^-$,
wherein
$R^1$ is H or $C(O)R^4$ in which $R^4$ is $NR^5R^6$ or $OR^7$, and $R^2$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;
or
$R^1$ and $R^2$ are independently selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;
or
$R^1$ and $R^2$ are linked to form an optionally substituted monocyclic or polycyclic ring system having 4 to 20 atoms including the carbonyl to which $R^1$ and $R^2$ are bonded and one or more of the carbons of the ring system is optionally replaced with a heteromoiety selected from O, S, N, $NR^8$ and $NR^8R^9$;
$R^{15}$ is selected from $C_{1-20}$alkyl, $C_{2-20}$alkenyl, $C_{2-20}$alkynyl, $C_{3-20}$cycloalkyl, aryl and heteroaryl, all of which are optionally substituted and one or more of the carbons in $C_{1-20}$alkyl, $C_{2-20}$alkenyl, $C_{3-20}$cycloalkyl or $C_{2-20}$alkynyl is optionally replaced with a heteromoiety selected from O, S, N, $NR^8$ and $NR^8R^9$;
M is a metal or metal-based radical;
c is an integer representing the number of the ligands $R^{15}$ required to fulfill the valency requirements of M;
$R^5$, $R^6$, $R^7$, $R^8$ and $R^9$ are independently selected from H, $C_{1-20}$alkyl, $C_{3-20}$cycloalkyl, aryl and heteroaryl, the latter 4 groups are optionally substituted; and
Y is an anionic counter ion.

Still further, within the scope of the present application is an aspect relating to a method of preparing an amine of formula VI:

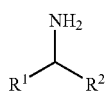

comprising reacting a compound of formula II:

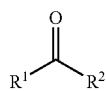

and a reducing agent in the presence of ammonia $NH_3$ or an ammonia equivalent of the formula $NH_4^+Y^-$,
wherein
$R^1$ is H or $C(O)R^4$ in which $R^4$ is $NR^6R^6$ or $OR^7$, and $R^2$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;
or
$R^1$ and $R^2$ are independently selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^5$ and $NR^8R^9$;
or
$R^1$ and $R^2$ are linked to form an optionally substituted monocyclic or polycyclic ring system having 4 to 20 atoms including the carbonyl to which $R^1$ and $R^2$ are bonded and one or more of the carbons of the ring system is optionally replaced with a heteromoiety selected from O, S, N, $NR^8$ and $NR^8R^9$; and $R^5$, $R^6$, $R^7$, $R^8$ and $R^9$ are independently selected from H, $C_{1-20}$alkyl, $C_{3-20}$cycloalkyl, aryl and heteroaryl, the latter 4 groups being optionally substituted; and
Y is an anionic counter ion.

It is an embodiment of the present application that the methods of preparing the compounds of the formulae I, IV and VI are performed in the presence of a catalyst, such as a transition metal catalyst. In a further embodiment, the catalyst comprises a chiral ligand and its use results in the preparation of enantiomerically enriched compounds of formulae I, IV and VI.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DETAILED DESCRIPTION OF THE APPLICATION

Definitions

The term "$C_{1-n}$alkyl" as used herein means straight or branched chain alkyl groups containing from one to n carbon atoms and includes, depending on the identity of n, methyl, ethyl, propyl, isopropyl, t-butyl, pentyl, hexyl, heptyl, octyl, nonyl, decyl, undecyl, dodecyl, hexadecyl, octadecyl, icosyl and the like and wherein n is an integer representing the maximum number of carbon atoms in the group.

The term "$C_{3-n}$cycloalkyl" as used herein means saturated cyclic or polycyclic alkyl groups containing from three to n carbon atoms and includes, depending on the identity of n, cyclopropyl, cyclobutyl, cyclopentyl, cyclohexyl, cycloheptyl, cyclooctyl, cyclononyl, cyclodecyl, cycloundecyl, cyclododecyl, cyclohexadecyl, cyclooctadecyl, cycloicosyl, adamantyl and the like, and wherein n is an integer representing the maximum number of carbon atoms in the group.

The term "$C_{1-n}$alkoxy" as used herein means straight or branched chain alkoxy groups containing from one to n carbon atoms and includes, depending on the identity of n, methoxy, ethoxy, propoxy, isopropoxy, t-butoxy, pentoxy, hexoxy, heptoxy, octoxy, nonoxy, decoxy, undecoxy, dodecoxy, hexadecoxy, octadecoxy, icosoxy and the like, and wherein n is an integer representing the maximum number of carbon atoms in the group.

The term "$C_{3-n}$cycloalkoxy" as used herein means saturated cyclic or polycyclic alkyoxy groups containing from three to n carbon atoms and includes, depending on the identity of n, cyclopropoxy, cyclobutoxy, cyclopentoxy, cyclohexoxy, cycloheptoxy, cyclooctoxy, cyclononoxy, cyclodecoxy, cycloundecoxy, cyclododecoxy, cyclohexadecoxy, cyclooctadecoxy, cycloicosoxy and the like, and wherein n is an integer representing the maximum number of carbon atoms in the group.

The term "$C_{2-n}$alkenyl" as used herein means straight or branched chain alkenyl groups containing from two to n carbon atoms and one to six double bonds and includes, depending on the identity of n, vinyl, allyl, 1-butenyl, 2-hexenyl and the like, and wherein n is an integer representing the maximum number of carbon atoms in the group.

The term "$C_{2-n}$alkynyl" as used herein means straight or branched chain alkynyl groups containing from 2 to n carbon atoms and one to six triple bonds and includes, depending on the identity of n, propargyl, 1-butynyl, 2-hexynyl and the like, and wherein n is an integer representing the maximum number of carbon atoms in the group.

The term "aryl" as used herein means a monocyclic or polycyclic carbocyclic ring system containing one or two aromatic rings and from 6 to 14 carbon atoms and includes phenyl, naphthyl, anthraceneyl, 1,2-dihydronaphthyl, 1,2,3,4-tetrahydronaphthyl, fluorenyl, indanyl, indenyl and the like.

The term "heteroaryl" as used herein means mono- or polycyclic heteroaromatic radicals containing from 5 to 14 atoms, of which 1 to 6 atoms are a heteroatom selected from nitrogen, oxygen and sulfur and includes furanyl, thienyl, pyrrolo, pyridyl, indolo, benzofuranyl and the like.

The term "halo" as used herein means halogen and includes chloro, fluoro, bromo and iodo.

The term "polycyclic" or "ring system" as used herein means a cyclic group containing more than one ring in its structure, and includes bicyclic, tricyclic, bridged and spiro ring systems and the like.

The term "halo-substituted $C_{1-20}$alkyl" as used herein means straight or branched chain, saturated alkyl radicals containing from one to n carbon atoms in which one or all of the hydrogen atoms have been replaced with a halogen, in particular fluorine, and includes (depending on the identity of "n") trifluoromethyl, pentafluoroethyl, fluoromethyl and the like, where the variable n is an integer representing the largest number of carbon atoms in the alkyl radical.

The term "halo-substituted $C_{1-20}$alkoxy" as used herein means straight or branched chain, saturated alkoxy radicals containing from one to n carbon atoms in which one or all of the hydrogen atoms have been replaced with a halogen, in particular fluorine, and includes (depending on the identity of "n") trifluoromethoxy, pentafluoroethoxy, fluoromethoxy and the like, where the variable n is an integer representing the largest number of carbon atoms in the alkoxy radical.

The term "one or more" as used herein means that from one to the maximum allowable substitutions are allowed.

The term "optionally substituted" means unsubstituted or substituted. When a group is substituted it may be substituted one or more times, one to five times, one to three times, one to two times or one time.

The present application includes combinations of groups and substituents that are permitted and would provide a stable chemical entity according to standard chemical knowledge as would be known to those skilled in the art.

The term "ammonia equivalent" as used here refers to a compound that reacts in situ to produce an equivalent of "$NH_3$" or ammonia.

The term "enantiomerically enriched" as used herein means a mixture of enantiomeric compounds that contains an excess of one enantiomer over the other(s).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Methods of the Application

Methods for the direct addition of a variety of trifluoroborate nucleophiles to carbonyl compounds, such as aldehydes and/or ketones, in the presence of ammonia have been shown to afford the corresponding primary, secondary or tertiary carbinamine compounds in moderate to excellent yields under mild reaction conditions. The methods have been shown to be simple and efficient in the incorporation of ammonia into the carbinamine end-products.

Accordingly, the present application relates to a method of preparing an amine of formula I:

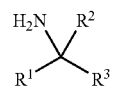

I comprising reacting a compound of formula II with a compound of formula III:

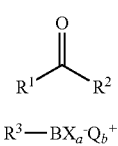

II

III in the presence of ammonia $NH_3$ or an ammonia equivalent of the formula $NH_4^+Y^-$,
wherein
$R^1$ is H or $C(O)R^4$ in which $R^4$ is $NR^5R^6$ or $OR^7$, and $R^2$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkynyl, $C_{3-20}$cycloalkyl or $C_{3-20}$cycloalkoxy is optionally replaced with a heteromoiety selected from O, S, N, $NR^8$ and $NR^6R^9$;
or
$R^1$ and $R^2$ are independently selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^6$;
or
$R^1$ and $R^2$ are linked to form an optionally substituted monocyclic or polycyclic ring system having 4 to 20 atoms including the carbonyl to which $R^1$ and $R^2$ are bonded and one or more of the carbons of the ring system is optionally replaced with a heteromoiety selected from O, S, N, $NR^8$ and $NR^8R^6$;
$R^3$ is selected from aryl, heteroaryl,

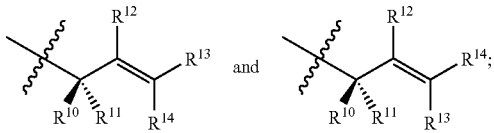

$R^{10}$ to $R^{14}$ are independently selected from H, $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, the latter 9 groups being optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;
$R^5$, $R^6$, $R^7$, $R^8$ and $R^9$ are independently selected from H, $C_{1-20}$alkyl, $C_{3-20}$cycloalkyl, aryl and heteroaryl with the latter 4 groups being optionally substituted,
X is an anionic ligand;
Y is an anionic counter ion;
Q is a cationic counter ion;
a is an integer representing the number of the anionic ligands X required to fulfill the valency requirements of B and Q; and
b is an integer representing the number of the cationic counter ions Q required to fulfill the valency requirements of X and B.

It is an embodiment of the application that, in the preparation of compounds of formula I, the compounds of formulae I and II include those in which $R^1$ is H or $C(O)R^4$ and that $R^4$ is $NR^5R^6$ or $OR^7$, in which $R^5$, $R^6$ and $R^7$ are independently selected from H, $C_{1-6}$alkyl and aryl, and $R^2$ is selected from $C_{1-10}$alkyl, aryl and heteroaryl, all of which are optionally substituted. In a particular embodiment of the application, $R^1$ in the compounds of the formulae I and II is H, $C(O)NH_2$ or $C(O)OCH_3$ and $R^2$ in the compounds of the formulae Ia, Ib and II is selected from methyl, ethyl, propyl, butyl, pentyl, hexyl, heptyl, phenyl, benzyl, furan, thiophene, thiazole, pyrrole, pyridyl and indole, all of which are optionally substituted. In a more particular embodiment of the application, $R^1$ in the compounds of the formulae I and II is H, $C(O)NH_2$ or $C(O)OCH_3$ and $R^2$ in the compounds of the formulae I and II is selected from methyl, ethyl, propyl, heptyl, phenyl, pyridyl and indole, all of which are optionally substituted.

In another embodiment of the application, in the preparation of compounds of formula I, $R^1$ and $R^2$ in the compounds of the formulae I and II are independently selected from $C_{1-10}$alkyl, aryl and heteroaryl, all of which are optionally substituted. Particularly, in an embodiment of the application, $R^1$ and $R^2$ in the compounds of the formulae I and II are independently selected from methyl, ethyl, propyl, butyl, pentyl, hexyl, heptyl, phenyl, benzyl, furan, thiophene, thiazole, pyrrole, pyridyl and indole, all of which are optionally substituted. More particularly, in an embodiment of the application, $R^1$ and $R^2$ in the compounds of the formulae I and II are independently selected from methyl, ethyl, phenyl, furan, thiazole, pyrrole and pyridyl, all of which are optionally substituted.

In yet another embodiment of the application, in the preparation of compounds of formula I, $R^1$ and $R^2$ in the compounds of the formulae I and II are linked to form an optionally substituted monocyclic or polycyclic ring system having 6 to 16 carbons including the carbonyl to which $R^1$ and $R^2$ are bonded. In a further embodiment of the application, one or more of the carbons of the ring system is optionally replaced with a heteroatom selected from O, S, N, $NR^8$ and $NR^8R^9$, in which $R^8$ and $R^9$ are independently selected from H, $C_{1-6}$alkyl and aryl. Particularly, in an embodiment of the application, $R^1$ and $R^2$ in the compounds of the formulae I and II are linked to form a ring system selected from cyclohexane, 2,3-dihydroindene, bicyclo[3.2.1]octane, bicyclo[2.2.1]heptane, bicyclo[2.2.1]octane, bicyclo[3.1.1]hept-2-ene and fluorene, all of which are optionally substituted, and one or more of the carbons of cyclohexane, 2,3-dihydroindene, bicyclo[2.2.1]heptane, bicyclo[2.2.1]octane, bicyclo[3.1.1]hept-2-ene and fluorene is optionally replaced with a heteroatom selected from O, S and $NR^8$, in which $R^8$ is H or $C_{1-6}$alkyl. More particularly, in an embodiment of the application, $R^1$ and $R^2$ in the compounds of the formulae I and II are linked to form a ring system selected from cyclohexane, 2,3-dihydroindene and bicyclo[2.2.1]heptane, all of which are optionally substituted, and one or more of the carbons of cyclohexane, 2,3-dihydroindene and bicyclo[2.2.1]heptane is optionally replaced with a heteroatom selected from O, S and $NR^8$, in which $R^8$ is H or $C_{1-6}$alkyl.

It is another embodiment of the application that, in the preparation of compounds of formula I, the optional substituents on $R^1$ and $R^2$ in the compounds of the formulae I and II are independently selected from OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl. In a further embodiment of the application, the optional substituents on $R^1$ and $R^2$ in the compounds of the formulae I and II are independently selected from F, Cl, Br, CN, $NO_2$, $CF_3$, $OCF_3$, $C_{1-4}$alkyl, $C_{1-4}$alkoxy, phenyl, benzyl, benzyloxy and $C(O)OC_{1-4}$alkyl.

It is a further embodiment of the present disclosure that, in the preparation of compounds of formula I, $R^3$ is selected from optionally substituted aryl,

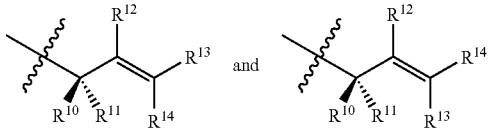

and $R^{10}$ to $R^{14}$ are independently selected from H, $C_{1-10}$alkyl, $C_{3-12}$cycloalkyl, aryl and heteroaryl, the latter 4 groups being optionally substituted, and one or more of the carbons in $C_{1-10}$alkyl or $C_{3-12}$cycloalkyl is optionally replaced with a heteromoiety selected from O, S, N, $NR^8$ and $NR^8R^9$ in which $R^8$ and $R^9$ are independently selected from H and $C_{1-6}$alkyl. In a particular embodiment of the application, $R^3$ is selected from optionally substituted phenyl,

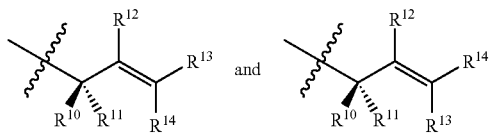

and $R^{10}$ to $R^{14}$ are independently selected from H and $C_{1-6}$alkyl. Still further, in an embodiment of the application, the optional substituents on $R^3$ in the compounds of the formulae I and III are independently selected from OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}alkyl)$, $N(C_{1-6}alkyl)(C_{1-6}alkyl)$, $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

When $R^3$ in the compound of formula III is selected from

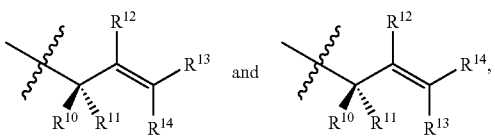

the (E) stereochemistry provides anti-homoallylic amine of formula I as the major product, where (Z) stereochemistry provides the syn-homoallylic amine of formula I as the major product. By "major product" it is mean that greater than about 90%, suitably greater than about 95%, more suitably greater than about 96%, of the product possesses the designated stereochemistry.

It is an embodiment of the application that, in the preparation of compounds of formula I, X is selected from F, Cl, Br and I. It is another embodiment of the application that Q is selected from Li, Na and K. In a more particular embodiment of the application, X is F, Q is K, a is 3 and b is 1.

In an embodiment of the application, the method is performed in the presence of ammonia. In yet another embodiment of the application, the method is performed in the presence of an ammonia salt $NH_4^+Y^-$, in which Y is an anionic ligand. In a further embodiment of the application, Y is selected from halo, $R^{16}COO$, $R^{16}SO_4$ and $BF_4$, in which $R^{16}$ is selected from $C_{1-10}$alkyl, $C_{3-20}$cycloalkyl, aryl and heteroaryl, all of which are optionally substituted. In an embodiment of the application, Y is Cl or Br. In a still further embodiment of the application, the optional substituents on $R^{16}$ are independently selected from OH, halo, CN, $NO_2$, phenyl, benzyl, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, $NH_2$, $NH(C_{1-6}alkyl)$, $N(C_{1-6}alkyl)(C_{1-6}alkyl)$, $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

In an embodiment of the application, the method of preparing compounds of formula I is performed in a suitable solvent. More particularly, the solvent is selected from selected from methanol, ethanol, propanol, butanol, toluene, tetrahydrofuran, acetonitrile, benzene, dioxane, methylene chloride, liquid ammonia, ionic liquids and mixtures thereof. Still more particularly, the solvent is methanol.

In one embodiment of the application, the method of preparing compounds of formula I is performed by combining an alcoholic solution of ammonia, or an ammonia equivalent in a suitable solvent, with the compound of formula II. The ammonia or ammonia equivalent is suitably used in molar excess amounts, for example about 5 to about 20 molar equivalents, relative to the amount of the compound of formula II. Once the ammonia or ammonia equivalent has reacted with the compound of formula II for a sufficient period of time (determinable by a person skilled in the art, for example by following the reaction using thin layer chromatography and observing the disappearance of the compound of formula II), the compound of formula III may be added to the combined solution of ammonia or ammonia equivalent and compound of formula II. The compound of formula III may be used in molar excess amounts, for example about 1.1 to about 5 molar equivalents, suitably about 1.2 to 2.5 molar equivalents, relative to the amount of the compound of formula II.

It is an embodiment of the application that the method is performed at room temperature or above or below room temperature, for example, at a temperature of from $-40°$ C. to $+100°$ C., suitably from $0°$ C. to $50°$ C., more suitably from $10°$ C. to $30°$ C. In an embodiment of the application, the method is performed at room temperature.

A person skilled in the art would appreciate that the reaction temperature and other conditions, such as reaction time, for the compounds of formula I may vary depending on a number of variables, including, but not limited to the structure of the starting materials (compounds of formulae II and III), the solvent and the reaction pressure. A person skilled in the art would be able to optimize the reaction temperature to obtain the best yields and overall performance of the reaction. Reaction progress may be monitored using known techniques, for example, thin layer chromatography, high performance liquid chromatography and/or NMR spectroscopy, to determine optimum reaction conditions.

The compounds of the formula I may optionally be isolated using standard methods known in the art, for example, by acid/base extraction methods. Further purification steps may be performed, for example, chromatography, and if $R^1$, $R^2$ and $R^3$ are different, chiral resolution. Chiral resolution of enantiomers may be performed, for example, by forming chiral esters or salts, followed by separation of the diastereomers using crystallization or chromatographic techniques, and liberation of the free amine.

Methods for the direct addition of a variety of nucleophilic organometalic reagents to carbonyl compounds, such as aldehydes and/or ketones, in the presence of ammonia have been shown to afford the corresponding primary, secondary or tertiary carbinamine compounds in moderate to excellent yields under mild reaction conditions. The methods have been shown to be simple and efficient in the incorporation of ammonia into the carbinamine end-products.

Accordingly, in another aspect, the present application relates to a method of preparing an amine of formula IV:

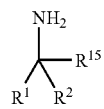

IV comprising reacting a compound of formula II with a compound of formula V:

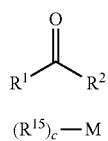

$$(R^{15})_c\text{—M} \quad \text{V}$$

in the presence of ammonia $NH_3$ or an ammonia equivalent of the formula $NH_4^+Y^-$,
wherein
$R^1$ is H or $C(O)R^4$ in which $R^4$ is $NR^5R^6$ or $OR^7$, and $R^2$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;
or
$R^1$ and $R^2$ are independently selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;
or
$R^1$ and $R^2$ are linked to form an optionally substituted monocyclic or polycyclic ring system having 4 to 20 atoms including the carbonyl to which $R^1$ and $R^2$ are bonded and one or more of the carbons of the ring system is optionally replaced with a heteromoiety selected from O, S, N, $NR^8$ and $NR^8R^9$;
$R^{15}$ is selected from $C_{1-20}$alkyl, $C_{2-20}$alkenyl, $C_{2-20}$alkynyl, $C_{3-20}$cycloalkyl, aryl and heteroaryl, all of which are optionally substituted and one or more of the carbons in $C_{1-20}$alkyl, $C_{2-20}$alkenyl, $C_{3-20}$cycloalkyl or $C_{2-20}$alkynyl is optionally replaced with a heteromoiety selected from O, S, N, $NR^8$ and $NR^8R^9$;
M is a metal or metal-based radical;
c is an integer representing the number of the ligands $R^{15}$ required to fulfill the valency requirements of M;
$R^5$, $R^6$, $R^7$, $R^8$ and $R^9$ are independently selected from H, $C_{1-20}$alkyl, $C_{3-20}$cycloalkyl, aryl and heteroaryl, the latter 4 groups are optionally substituted; and
Y is an anionic ligand.

It is an embodiment of the application that, in the method of preparing a compound of formula IV, $R^1$ in the compounds of the formulae II and IV is H or $C(O)R^4$ in which $R^4$ is $NR^5R^6$ or $OR^7$, and $R^2$ in the compounds of the formulae II and IV is selected from $C_{1-10}$alkyl, aryl and heteroaryl, all of which are optionally substituted. Particularly, in an embodiment of the application, $R^1$ in the compounds of the formulae II and IV is H, and $R^2$ in the compounds of the formulae II and IV is selected from methyl, ethyl, propyl, butyl, pentyl, hexyl, heptyl, phenyl, benzyl, furan, thiophene, thiazole, pyrrole, pyridyl and indole, all of which are optionally substituted. More particularly, in an embodiment of the application, $R^1$ in the compounds of the formulae II and IV is H, and $R^2$ in the compounds of the formulae II and IV is optionally substituted phenyl.

It is another embodiment of the application that, in the method of preparing a compound of formula IV, $R^1$ and $R^2$ in the compounds of the formulae II and IV are independently selected from $C_{1-10}$alkyl, aryl and heteroaryl, all of which are optionally substituted. More particularly, in an embodiment of the application, $R^1$ and $R^2$ in the compounds of the formulae II and IV are independently selected from methyl, ethyl, propyl, butyl, pentyl, hexyl, heptyl, phenyl, benzyl, furan, thiophene, thiazole, pyrrole, pyridyl and indole, all of which are optionally substituted.

In yet another embodiment of the application, $R^1$ and $R^2$ in the compounds of the formulae II and IV are linked to form an optionally substituted monocyclic or polycyclic ring system having 6 to 16 carbons including the carbonyl to which $R^1$ and $R^2$ are bonded. In a further embodiment of the application, one or more of the carbons of the ring system is optionally replaced with a heteromoiety selected from O, S, N, $NR^8$ and $NR^8R^9$, in which $R^8$ and $R^9$ are independently selected from H, $C_{1-6}$alkyl and aryl. In a still further embodiment of the application, $R^1$ and $R^2$ in the compounds of the formulae II and IV are linked to form a ring system selected from cyclohexane, 2,3-dihydroindene, bicyclo[3.2.1]octane, bicyclo[2.2.1]heptane, bicyclo[2.2.1]octane, bicyclo[3.1.1]hept-2-ene and fluorene, all of which are optionally substituted and one or more of the carbons of cyclohexane, 2,3-dihydroindene, bicyclo[3.2.1]octane, bicyclo[2.2.1]heptane, bicyclo[2.2.1]octane, bicyclo[3.1.1]hept-2-ene and fluorene is optionally replaced with a heteromoiety selected from O, S, and $NR^8$, in which $R^9$ is H or $C_{1-6}$alkyl.

In an embodiment of the application, in the method of preparing a compound of formula IV the optional substituents on $R^1$ and $R^2$ in the compounds of the formulae II and IV are independently selected from OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)$(C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl. More particularly, in an embodiment of the application, the optional substituents on $R^1$ and $R^2$ in the compounds of the formulae II and IV are independently selected from F, Cl, Br, CN, $NO_2$, $CF_3$, $OCF_3$, $C_{1-4}$alkyl, $C_{1-4}$alkoxy, phenyl, benzyl, benzyloxy and $C(O)OC_{1-4}$alkyl.

It is an embodiment of the application that, in the method of preparing a compound of formula IV, $(R^{15})_c$-M is an organometallic reagent, for example a Grignard reagent, an organozinc reagent, an organolithium reagent, an organosodium reagent and an organocuprate reagent. Particularly, in an embodiment of the application, the organometallic reagent is a Grignard reagent or an organozinc reagent. In a further embodiment of the application, M is MgBr and c is 1. In yet another embodiment of the application, M is Zn and c is 2.

It is an embodiment of the application that, in the method of preparing a compound of formula IV, $R^{15}$ in the compounds of the formulae IV and V is selected from $C_{1-10}$alkyl, aryl and heteroaryl, all of which are optionally substituted. In a further embodiment of the application, one or more of the carbons in $C_{1-10}$alkyl is optionally replaced with a heteromoiety selected from O, S, N, $NR^8$ and $NR^8R^9$ in which $R^8$ and $R^9$ are independently selected from H and $C_{1-6}$alkyl. Particularly, in an embodiment of the application, $R^{15}$ in the compounds of the formulae IV and V is $C_{1-6}$alkyl or aryl, both of which are optionally substituted. More particularly, in an embodiment of the application, $R^{15}$ in the compounds of the formulae IV and V is optionally substituted phenyl.

In an embodiment of the application, the optional substituents on $R^{15}$ in the compounds of the formulae IV and V are selected from OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl. In a further embodiment of the application, the optional substituents on $R^{15}$ in the compounds of the formulae IV and V are selected from F, Cl, Br, CN, $NO_2$, $CF_3$, $OCF_3$, $C_{1-4}$alkoxy, phenyl, benzyl, benzyloxy and $C(O)OC_{1-4}$alkyl.

In an embodiment of the application, the method of preparing a compound of formula IV, is performed in the presence of ammonia. In yet another embodiment of the application, the method is performed in the presence of an ammonia salt $NH_4^+Y^-$, in which Y is an anionic counter ion. In a further embodiment of the application, Y is selected from halo, $R^{16}COO$, $R^{16}SO_4$ and $BF_4$, in which $R^{16}$ is selected from $C_{1-10}$alkyl, $C_{3-20}$cycloalkyl, aryl and heteroaryl, all of which are optionally substituted. In an embodiment of the application, Y is Cl or Br. In a still further embodiment of the application, the optional substituents on $R^{16}$ are independently selected from OH, halo, CN, $NO_2$, phenyl, benzyl, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

In an embodiment of the application, the method of preparing compounds of formula IV is performed in a suitable solvent. More particularly, the solvent is selected from selected from methanol, ethanol, propanol, butanol, toluene, tetrahydrofuran, acetonitrile, benzene, dioxane, methylene chloride, liquid ammonia, ionic liquids and mixtures thereof.

In one embodiment of the application, the method of preparing compounds of formula IV is performed by combining an alcoholic solution of ammonia, or an ammonia equivalent in a suitable solvent, with the compound of formula II, suitably at or about room temperature, although the temperature may be varied to optimize reaction conditions as would be known to a person skilled in the art. The ammonia or ammonia equivalent is suitably used in molar excess amounts, for example 5 to about 20 molar equivalents, relative to the amount of the compound of formula II. Once the ammonia or ammonia equivalent has reacted with the compound of formula II for a sufficient period of time (determinable by a person skilled in the art, for example by following the reaction using thin layer chromatography and observing the disappearance of the compound of formula II), volatile materials are removed and the compound of formula III may then be added to the combined solution of ammonia and compound of formula II. The compound of formula III may be used in molar excess amounts, for example about 1.1 to about 5 molar equivalents, suitably about 1.2 to 2.5 molar equivalents, relative to the amount of the compound of formula II. As many of the compounds of formula III are air and moisture sensitive, as well as highly reactive, the addition of the compounds of formula III is desirably done at reduced temperatures, for example, at about $-100°$ C. to about $-50°$ C. The final reaction mixture may be warmed, for example to room temperature, after the addition of the compound of formula III is complete.

A person skilled in the art would appreciate that the reaction temperature and other conditions, such as reaction time, for the preparation of compounds of formula IV may vary depending on a number of variables, including, but not limited to the structure of the starting materials (compounds of formulae II and V), the solvent and the reaction pressure. A person skilled in the art would be able to optimize the reaction temperature to obtain the best yields and overall performance of the reaction. Reaction progress may be monitored using known techniques, for example, thin layer chromatography, high performance liquid chromatography and/or NMR spectroscopy, to determine optimum reaction conditions.

The compounds of the formula IV may optionally be isolated using standard methods known in the art, for example, by acid/base extraction methods. Further purification steps may be performed, for example, chromatography, and if $R^1$, $R^2$ and $R^{15}$ are different, chiral resolution. Chiral resolution of enantiomers may be performed, for example, by forming chiral esters or salts, followed by separation of the diastereomers using crystallization or chromatographic techniques, and liberation of the free amine.

It has also been found that carbonyl compounds may be reductively aminated in the presence of a hydrogen sounds and ammonia to provide the corresponding amine compounds in moderate to excellent yields under mild reaction conditions.

Accordingly, within the scope of the present application is an aspect relating to a method of preparing an amine of formula VI:

VI comprising reacting a compound of formula II:

II and a reducing agent in the presence of ammonia $NH_3$ or an ammonia equivalent of the formula $NH_4^+Y^-$:
wherein
$R^1$ is H or $C(O)R^4$ in which $R^4$ is $NR^5R^6$ or $OR^7$, and $R^2$ is selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;
or
$R^1$ and $R^2$ are independently selected from $C_{1-20}$alkyl, $C_{1-20}$alkoxy, $C_{2-20}$alkenyl, $C_{2-20}$alkynyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{2-20}$alkynyl, $C_{3-20}$cycloalkyl or $C_{3-20}$cycloalkoxy is optionally replaced with a heteromoiety selected from O, S, N, $NR^8$ and $NR^8R^9$;
or
$R^1$ and $R^2$ are linked to form an optionally substituted monocyclic or polycyclic ring system having 4 to 20 atoms including the carbonyl to which $R^1$ and $R^2$ are bonded and one or more of the carbons of the ring system is optionally replaced with a heteromoiety selected from O, S, N, $NR^8$ and $NR^8R^9$; and $R^5$, $R^6$, $R^7$, $R^8$ and $R^9$ are independently selected from H, $C_{1-20}$alkyl, $C_{3-20}$cycloalkyl, aryl and heteroaryl, the latter 4 groups being optionally substituted; and
Y is an anionic counter ion.

It is an embodiment of the application that, in the method of preparing compounds of formula VI, $R^1$ in the compounds of the formulae II and VI is H or C(O)$R^4$ in which $R^4$ is NR$^5$R$^6$ or OR$^7$, and $R^2$ in the compounds of the formulae II and VI is selected from $C_{1-10}$alkyl, aryl and heteroaryl, all of which are optionally substituted. Particularly, in an embodiment of the application, $R^1$ in the compounds of the formulae II and VI is H, and $R^2$ in the compounds of the formulae II and VI is selected from methyl, ethyl, propyl, butyl, pentyl, hexyl, heptyl, phenyl, benzyl, furan, thiophene, thiazole, pyrrole, pyridyl and indole, all of which are optionally substituted. More particularly, in an embodiment of the application, $R^1$ in the compounds of the formulae II and VI is H, and $R^2$ in the compounds of the formulae II and VI is optionally substituted phenyl.

It is another embodiment of the application that, in the method of preparing compounds of formula VI, $R^1$ and $R^2$ in the compounds of the formulae II and VI are independently selected from $C_{1-10}$alkyl, aryl and heteroaryl, all of which are optionally substituted. In a further embodiment of the application, $R^1$ and $R^2$ in the compounds of the formulae II and VI are independently selected from methyl, ethyl, propyl, butyl, pentyl, hexyl, heptyl, phenyl, benzyl, furan, thiophene, thiazole, pyrrole, pyridyl and indole, all of which are optionally substituted. In a still further embodiment of the application, $R^1$ in the compounds of the formulae II and VI is methyl and $R^2$ in the compounds of the formulae II and VI is optionally substituted phenyl.

In yet another embodiment of the application, in the method of preparing compounds of formula VI, $R^1$ and $R^2$ in the compounds of the formulae II and VI are linked to form an optionally substituted monocyclic or polycyclic ring system having 6 to 16 carbons including the carbonyl to which $R^1$ and $R^2$ are bonded. Further, in an embodiment of the application, one or more of the carbons of the ring system is optionally replaced with a heteromoiety selected from O, S, N, NR$^8$ and NR$^8$R$^9$, in which $R^8$ and $R^9$ are independently selected from H, $C_{1-6}$alkyl and aryl. Still further, in an embodiment of the application, $R^1$ and $R^2$ in the compounds of the formulae II and VI are independently selected from methyl, ethyl, propyl, butyl, pentyl, hexyl, heptyl, phenyl, benzyl, furan, thiophene, thiazole, pyrrole, pyridyl and indole, all of which are optionally substituted. More particularly, in an embodiment of the application, $R^1$ and $R^2$ in the compounds of the formulae II and VI are linked to form a ring system selected from cyclohexane, 2,3-dihydroindene, bicyclo[3.2.1]octane, bicyclo[2.2.1]heptane, bicyclo[2.2.1]octane, bicyclo[3.1.1]hept-2-ene and fluorene, all of which are optionally substituted and one or more of the carbons of cyclohexane, 2,3-dihydroindene, bicyclo[3.2.1]octane, bicyclo[2.2.1]heptane, bicyclo[2.2.1]octane, bicyclo[3.1.1]hept-2-ene and fluorene is optionally replaced with a heteromoiety selected from O, S, and NR$^8$, in which $R^8$ is H or $C_{1-6}$alkyl.

In an embodiment of the application, in the method of preparing compounds of formula VI, the optional substituents on $R^1$ and $R^2$ in the compounds of the formulae II and VI are independently selected from OH, halo, CN, NO$_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl ($C_{1-4}$alkoxy), heteroaryl, heteroaryloxy, heteroaryl ($C_{1-4}$alkoxy), NH$_2$, NH($C_{1-6}$alkyl), N($C_{1-6}$alkyl)($C_{1-6}$alkyl), C(O)$C_{1-6}$alkyl, C(O)O$C_{1-6}$alkyl, SO$_2$$C_{1-6}$alkyl, SO$_2$NH$_2$, SO$_2$NH$C_{1-6}$alkyl and S$C_{1-4}$alkyl. Particularly, in an embodiment, the optional substituents on $R^1$ and $R^2$ in the compounds of the formulae II and VI are independently selected from F, Cl, Br, CN, NO$_2$, CF$_3$, OCF$_3$, $C_{1-4}$alkyl, $C_{1-4}$alkoxy, phenyl, benzyl, benzyloxy and C(O)O$C_{1-4}$alkyl. More particularly, the optional substituents on $R^1$ and $R^2$ in the compounds of the formulae II and VI are independently selected from F, Cl and Br.

It is an embodiment of the application that, in the method of preparing compounds of formula VI, the reducing agent is selected from hydride reagents and hydrogenation conditions. In a further embodiment, the hydride reagent is selected from lithium aluminum hydride and derivatives thereof, sodium borohydride and derivatives thereof, diborane and 9-BBN. Particularly, in an embodiment of the application, the hydride reagent is sodium borohydride. In another embodiment the hydrogenation conditions comprise hydrogen gas and a catalyst, for example, a transition metal catalyst. Further, in an embodiment of the application, the metal is selected from platinum, palladium, nickel and rhodium. Still further, in an embodiment of the application, the catalyst is palladium on activated carbon.

In an embodiment of the application, the method is performed in the presence of ammonia. In yet another embodiment of the application, the method is performed in the presence of an ammonia salt NH$_4$$^+$Y$^-$, in which Y is an anionic ligand. In a further embodiment of the application, Y is selected from halo, $R^{16}$COO, $R^{16}$SO$_4$ and BF$_4$, in which $R^{16}$ is selected from $C_{1-10}$alkyl, $C_{3-20}$cycloalkyl, aryl and heteroaryl, all of which are optionally substituted. In an embodiment of the application, Y is Cl or Br. In a still further embodiment of the application, the optional substituents are independently selected from OH, halo, CN, NO$_2$, phenyl, benzyl, $C_{1-6}$alkyl, halo-substituted $C_{1-6}$alkyl, halo-substituted $C_{1-6}$alkoxy, $C_{1-6}$alkoxy, halo-substituted $C_{1-6}$alkoxy, $C_{2-6}$alkenyl, $C_{2-6}$alkenyloxy, NH$_2$, NH($C_{1-6}$alkyl), N($C_{1-6}$alkyl)($C_{1-6}$alkyl), C(O)$C_{1-6}$alkyl, C(O)O$C_{1-6}$alkyl, SO$_2$$C_{1-6}$alkyl, SO$_2$NH$_2$, SO$_2$NH$C_{1-6}$alkyl and S$C_{1-4}$alkyl.

In an embodiment of the application, the method of preparing compounds of formula VI is performed in a suitable solvent. More particularly, the solvent is selected from selected from methanol, ethanol, propanol, butanol, toluene, tetrahydrofuran, acetonitrile, benzene, dioxane, methylene chloride, liquid ammonia, ionic liquids and mixtures thereof.

In one embodiment of the application, the method of preparing compounds of formula VI is performed by combining an alcoholic solution of ammonia, or an ammonia equivalent in a suitable solvent, with the compound of formula II, suitably at or about room temperature, although the temperature may be varied to optimize reaction conditions as would be known to a person skilled in the art. The ammonia or ammonia equivalent is suitably used in molar excess amounts, for example about 5 to about 20 molar equivalents, relative to the amount of the compound of formula II. Once the ammonia or ammonia equivalent has been reacted with the compound of formula II for a sufficient period of time (determinable by a person skilled in the art, for example by following the reaction using thin layer chromatography and observing the disappearance of the compound of formula II), the reducing agent may be added. When hydrogen is used as the reducing agent, it is an embodiment that the method of preparing compounds of formula VI is performed at a pressure of from 1 atm to 10 atm. More suitably, in an embodiment of the application, the method is performed at a pressure of from 1 atm to 5 atm.

A person skilled in the art would appreciate that the reaction temperature and other conditions, such as reaction time, for the preparation of the compounds of formula VI may vary depending on a number of variables, including, but not limited to the structure of the starting materials (compounds of formulae II), the solvent and the reaction pressure. A person skilled in the art would be able to optimize the reaction temperature to obtain the best yields and overall performance of the reaction. Reaction progress may be monitored using known techniques, for example, thin layer chromatography, high performance liquid chromatography and/or NMR spectroscopy, to determine optimum reaction conditions.

The compounds of the formulae VI may optionally be isolated using standard methods known in the art, for example, by acid/base extraction methods. Further purification steps may be performed, for example, chromatography, and if $R^1$ and $R^2$ are different, chiral resolution. Chiral resolution of enantiomers may be performed, for example, by forming chiral esters or salts, followed by separation of the diastereomers using crystallization or chromatographic techniques, and liberation of the free amine.

It is an embodiment of the application that the methods for preparing compounds of formula I, IV and/or VI are performed in the presence of a catalyst, in particular a transition metal catalyst. Particularly, in an embodiment of the application, the catalyst is any of the well-known transition metal catalysts. In a further embodiment of the application, the metal is selected from rhodium, ruthenium, iridium, copper, platinum, palladium and nickel. In a still further embodiment of the application, the metal is rhodium. The catalyst may be included in the method, for example, by adding it along with the compound of formula III, V, hydride reagent or hydrogen either by a separate addition or in a combined solution.

In an embodiment of the present application, when a catalyst is used, it is added in amounts of about 1 mol % to about 20 mol %, suitably about 5 mol % to about 10 mol %, based on the amount of the aldehyde.

In another embodiment of the application, the metal catalyst possesses at least one chiral or achiral ligand. In another embodiment, the ligand is a phosphine, diphosphine, aminophosphine, carbene, amine or oxazoline ligand. Transition metal catalysts containing chiral ligands are well known in the art and include those used for stereoselective hydrogenations, transmetalation and other bond forming reactions [a] *Transition metals for organic synthesis*, ed. M. Belier and C. Bolm, Wiley-VCH, New York, 2nd edn, 2005; b) J. Tsuji in *Transition metal reagents and catalysts: innovations in organic synthesis*, John Wiley & Sons, New York, 2000]. By performing the methods described herein in the presence of a chiral catalyst, stereoselective additions of the compounds of formula III to the compounds of formula II, of the compounds of formulae V to the compounds of formula II, and of reduction of the compounds of formula II are achieved. Accordingly, compounds of formulae I, IV and VI may be prepared in enantioselective and/or diastereoselective manner. In an embodiment, when a transition metal catalysts comprising a chiral ligand is used, one enantiomer or diastereomer will be present in an amount greater than 50%. In a further embodiment, one enantiomer or diastereomer will be present in an amount greater than 60%. In another embodiment, one enantiomer or diastereomer will be present in an amount greater than 70%. In a further embodiment, one enantiomer or diastereomer will be present in an amount greater than 80%. In yet a further embodiment, one enantiomer or diastereomer will be present in an amount greater than 90%. In another embodiment, one enantiomer or diastereomer will be present in an amount greater than 95%. In an embodiment, one enantiomer or diastereomer will be present in an amount greater than 99%.

The following non-limiting examples are illustrative of the present application:

EXAMPLES

Materials and Methods

All ketones in liquid form were distilled prior to use. All ketones in solid form were used as received. All other reagents were used as received (Aldrich, Acros, Strem). Methanol was dried over magnesium methoxide and distilled prior to use.

Melting points were uncorrected and were measured on a Fisher-Johns melting point apparatus. $^1$H and $^{13}$C NMR were recorded at 300 or 500 MHz and 75 or 125 MHz respectively on a Bruker Spectrospin 300 or 500 MHz spectrometer. Proton chemical shifts were internally referenced to the residual proton resonance in CDCl$_3$ ($\delta$ 7.26). Carbon chemical shifts were internally referenced to the deuterated solvent signals in CDCl$_3$ ($\delta$ 77.00). Infrared spectra were obtained on a Bruker VECTOR22 FT-IR spectrometer. HRMS-Cl and HRMS-ESI were performed on a Waters/Micromass GCT time-of-flight mass spectrometer and a Waters/Micromass Q-TOF Global quadrupole time-of-flight mass spectrometer respectively.

Example 1

General Procedure for the Allylation of Aldehydes with Potassium Allyltrifluoroborate in the Presence of Ammonia A solution of ammonia in methanol (ca. 7N in MeOH, 3.0 mL) was added to the aldehyde (0.5 mmol). The resulting solution was stirred for 15 minutes at room temperature, followed by the addition of potassium allyltrifluoroborate (2a) (222 mg, 1.5 mmol) and water (0.6 mL). The reaction mixture was subsequently stirred for 1 hour at room temperature. The volatiles were removed in vacuo and the residue re-dissolved in Et$_2$O (15 mL). Aqueous HCl (1N, 15 mL) was then added dropwise. The biphasic mixture was vigorously shaken, and the layers were separated. The acidic aqueous layer was washed with Et$_2$O (3×15 mL), and made basic by the addition of solid NaOH (ca. 5 g). The aqueous layer was then extracted with CH$_2$Cl$_2$ (3×15 mL). The combined organic extracts were dried with Na$_2$SO$_4$, filtered and concentrated in vacuo to afford the desired secondary carbinamine (3).

(i) Undec-1-en-4-amine (3a)

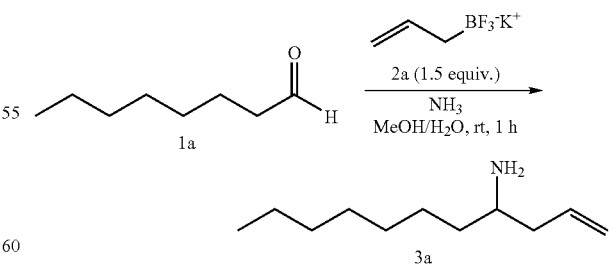

(3a) was isolated as a clear, colorless oil: $^1$H NMR (CDCl$_3$, 300 MHz) $\delta$ 5.82-5.65 (1H, m), 5.09-4.98 (2H, m), 2.77-2.68 (1H, m), 2.23-2.12 (1H, m), 1.99-1.88 (1H, m), 1.43-1.15 (14H, m), 0.84 (3H, t, J=7.0 Hz); $^{13}$C NMR (CDCl$_3$, 75 MHz) $\delta$ 135.92, 117.06, 50.53, 42.56, 27.65, 31.77, 29.65, 29.23, 26.19, 22.58, 14.01; HRMS (CI) m/z calcd. for $C_{11}H_{24}N$ (MH$^+$) 170.1909, found 170.1905.

(ii) 2,2-Dimethylhex-5-en-3-amine (3b)

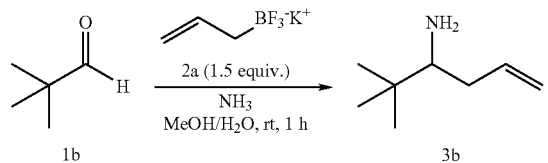

(3b) was isolated as a clear, colorless oil: $^1$H NMR (CDCl$_3$, 500 MHz) δ 5.83-5.73 (1H, m), 5.06 (1H, dd, J=17.0, 1.5 Hz), 5.04 (1H, dd, J=10.0, 1.5 Hz), 2.42 (1H, dd, J=10.5, 2.5 Hz), 2.38-2.30 (1H, m), 1.76-1.67 (1H, m), 1.11 (2H, br s), 0.87 (9H, s); $^{13}$C NMR (CDCl$_3$, 125 MHz) δ 137.71, 116.62, 59.47, 36.87, 26.09; HRMS (CI) m/z calcd. for $C_8H_{18}N$ (MH$^+$) 128.1439, found 128.1437.

(iii) Compound (3c)

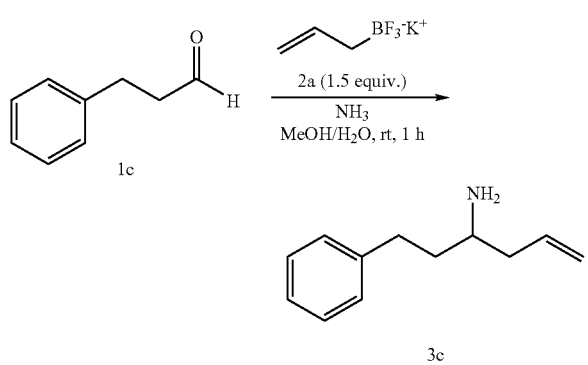

(iv) 1-(Benzyloxy)pent-4-en-2-amine (3d)

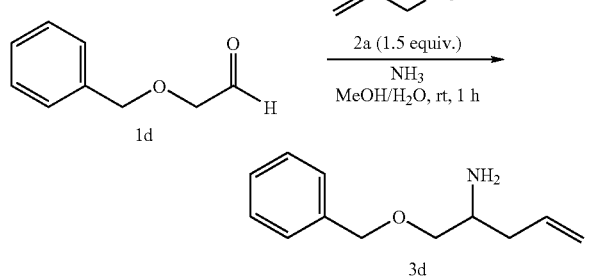

(3d) was isolated as a clear, colorless oil: $^1$H NMR (CDCl$_3$, 300 MHz) δ 7.32-7.20 (5H, m), 5.84-5.67 (1H, m), 5.12-5.00 (2H, m), 4.83 (2H, s), 3.41 (1H, dd, J=9.0, 4.5 Hz), 3.24 (1H, dd, J=9.0, 7.5 Hz), 3.08-2.97 (1H, m), 2.25-2.15 (1H, m), 2.08-1.94 (1H, m), 1.37 (2H, br s); $^{13}$C NMR (CDCl$_3$, 75 MHz) δ 138.09, 134.98, 128.10, 127.35, 127.32, 117.16, 75.07, 72.95, 50.15, 38.59; HRMS (ESI) m/z calcd. for $C_{12}H_{18}NO$ (MH$^+$) 192.1388, found 192.1384.

(v) Compound (3e)

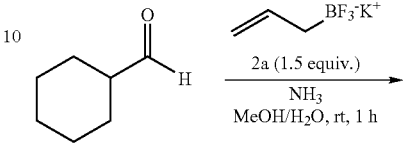

(vi) 1-(4-Methoxyphenyl)but-3-en-1-amine (3f)

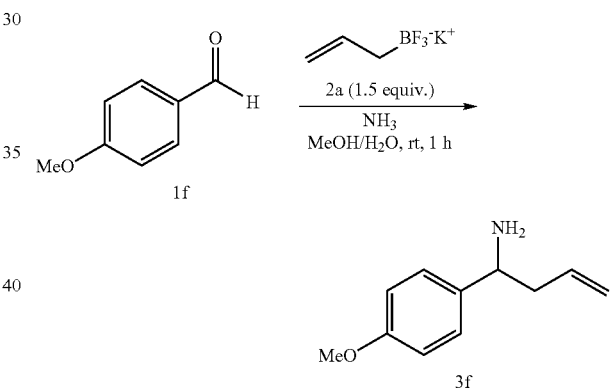

3f was isolated as a clear, colorless oil: $^1$H NMR (CDCl$_3$, 300 MHz) δ 7.23 (2H, d, J=8.5 Hz), 6.84 (2H, d, J=8.5 Hz), 5.80-5.64 (1H, m), 5.13-5.00 (2H, m), 3.92 (1H, dd, J=8.0, 5.5 Hz), 3.76 (3H, s), 2.46-2.24 (2H, m), 1.48 (2H, br s); $^{13}$C NMR (CDCl$_3$, 75 MHz) δ 158.41, 137.89, 135.49, 127.18, 117.30, 113.60, 5.08, 54.65, 44.17; HRMS (CI) m/z calcd. for $C_{11}H_{16}NO$ (MH$^+$) 178.1232, found 178.1227.

(vii) Compound (3g)

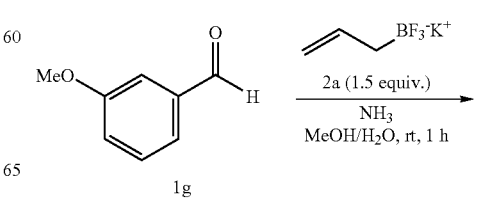

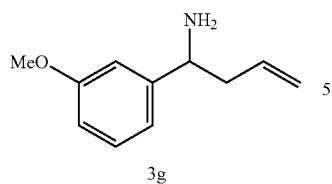
3g
(viii) Compound (3h)
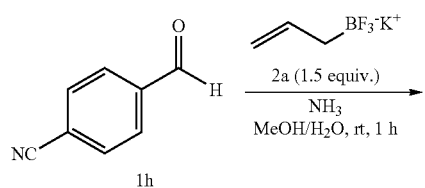
(ix) Compound (3i)
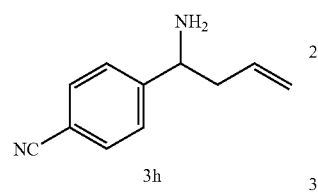
3h
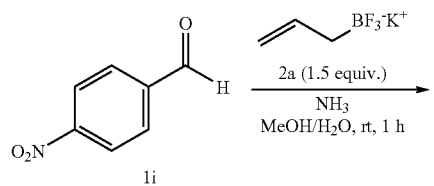
(x) 1-(1H-Indol-3-yl)but-3-en-1-amine (3j)
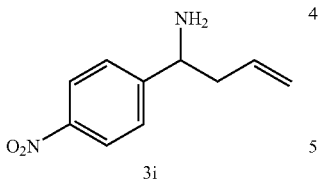
3i
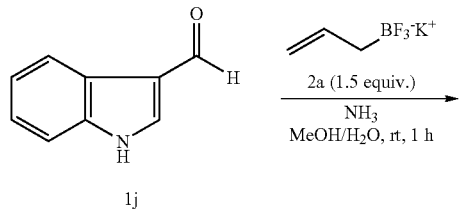
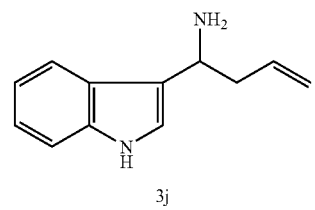
3j
3j was isolated as a clear, colorless oil: $^1$H NMR (CDCl$_3$, 300 MHz) δ 8.94 (1H, br s), 7.73 (1H, d, J=7.5 Hz), 7.31 (1H, d, J=8.0 Hz), 7.24-7.10 (2H, m), 7.02 (1H, d, J=2.0 Hz), 5.96-5.80 (1H, m), 5.25-5.10 (2H, m), 4.41 (1H, dd, J=8.0, 5.0 Hz), 2.80-2.69 (1H, m), 2.60-2.47 (1H, m), 1.80 (2H, br s); $^{13}$C NMR (CDCl$_3$, 75 MHz) δ 136.47, 135.83, 125.83, 121.77, 120.66, 120.26, 119.10, 118.95, 117.38, 111.29, 47.91, 42.98.
(xi) Compound (3k)
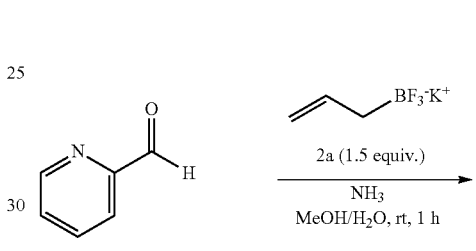
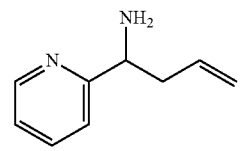
3k
(xii) 1-(Furan-2-yl)but-3-en-1-amine (3l)
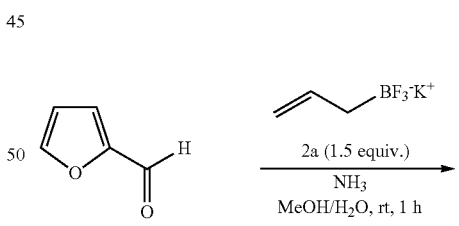
3l
3l isolated as a clear, colorless oil: $^1$H NMR (300 MHz, CDCl$_3$) δ 7.34 (1H, dd, J=2.0, 1.0 Hz), 6.26 (1H, dd, J=3.0, 2.0 Hz, 1H), 6.10 (1H, dd, J=3.0, 1.0 Hz), 5.74 (1H, dddd, J=17.0, 10.0, 7.5, 6.5 Hz), 5.16-5.08-5.00 (m, 2H), 3.98 (1H, dd, J=8.0, 5.5 Hz), 2.62-2.50 (1H, m), 2.45-2.32 (1H, m), 1.56
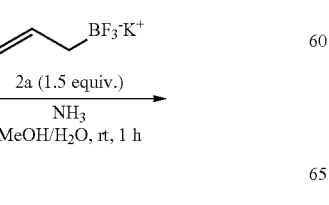

(2H, br s); $^{13}$C NMR (75 MHz, CDCl3) δ 158.55, 141.31, 134.71, 117.94, 110.07, 104.45, 49.23, 40.92.

(xiii) 1-(Thiophen-2-yl)but-3-en-1-amine (3m)

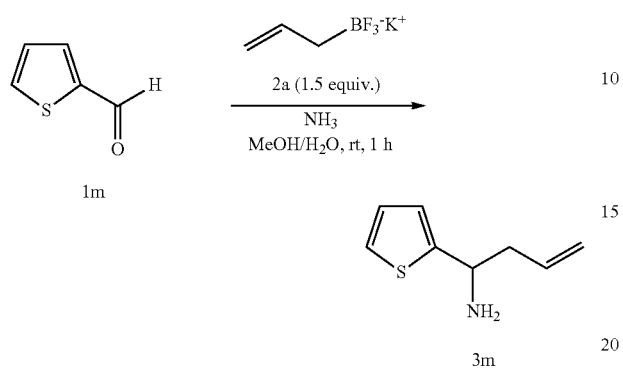

3m isolated as a clear, colorless oil: $^1$H NMR (300 MHz, CDCl$_3$) δ 7.21 (1H, dd, J=5.0, 1.5 Hz), 6.95-6.88 (2H, m), 5.77 (1H, dddd, J=17.0, 10.0, 7.5, 6.5 Hz), 5.13-5.08 (2H, m), 4.25 (1H, dd, J=8.0, 5.0 Hz), 2.63-2.55 (1H, m), 2.45-2.36 (1H, m), 1.62 (2H, br s); $^{13}$C NMR (75 MHz, CDCl$_3$) δ 150.79, 134.80, 126.51, 123.63, 122.68, 118.19, 51.34, 44.74.

Discussion:

The addition of potassium allyltrifluoroborate 2a to aldehydes, when first pretreated with ammonia, has been found to lead cleanly and efficiently to the formation of the corresponding secondary carbinamines. The results are shown in Table 1. The advantages of using 2a over the known allyl pinacol boronate [M. Sugiura, K. Hirano and S. Kobayashi, *J. Am. Chem. Soc.*, 2004, 126, 7182-7183; S. Kobayashi, K. Hirano and M. Sugiura, *J. Chem. Commun.*, 2005, 104-105; and M. Sugiura, C. Mori and S. Kobayashi, *J. Am. Chem. Soc.*, 2006, 128, 11038-11039] include the much greater stability and easier handling of the reagent. The present inventors have varied a number of reaction parameters to arrive at the following optimized conditions: 1.5 eq. of the trifluoroborate salt 2a in methanolic ammonia/water mixture, 10 eq. of NH$_3$. Water was added to dissolve 5a and it did not prove detrimental to the overall outcome of the reaction. As can be seen from Table 1, a wide variety of aldehydes were successfully allylated under these mild reaction conditions, including aliphatic (entries 1 to 5), aromatic (entries 6 to 9) and heteroaromatic (entries 10 and 11). The resulting secondary carbinamines were easily isolated and uniformly obtained in high yields through standard acid-base extraction, and did not require any subsequent chromatographic purification.

Example 2

General Procedure for the Crotylation of Aldehydes with Potassium (E) or (Z)-Crotyltrifluoroborate in the Presence of Ammonia A solution of ammonia in methanol (ca. 7N in MeOH, 3.0 mL) was added to the aldehyde (0.5 mmol). The resulting solution was stirred for 15 minutes at room temperature, followed by the addition of potassium crotyltrifluoroborate (2b or 2c) (392 mg, 1.5 mmol) and water (0.6 mL). The reaction mixture was subsequently stirred for 2 hours at room temperature. The volatiles were removed in vacuo and the residue redissolved in Et$_2$O (15 mL). Aqueous HCl (1N, 15 mL) was then added dropwise. The biphasic mixture was vigorously shaken, and the layers were separated. The acidic aqueous layer was washed with Et$_2$O (3×15 mL), and made basic by the addition of solid NaOH (ca. 5 g). The aqueous layer was then extracted with CH$_2$Cl$_2$ (3×15 mL). The combined organic extracts were dried with Na$_2$SO$_4$, filtered and concentrated in vacuo to afford the desired secondary carbinamine (4).

(i) (2S*,3S*)-1-(Benzyloxy)-3-methylpent-4-en-2-amine (4a)

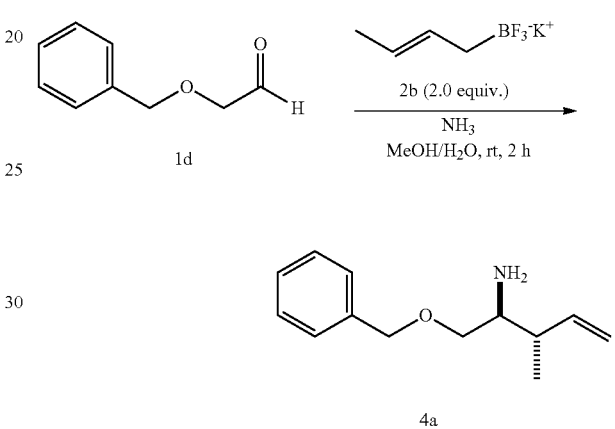

4a was isolated as a clear, colorless oil: $^1$H NMR (CDCl$_3$, 300 MHz) δ 7.35-7.22 (5H, m), 5.78-5.65 (1H, m), 5.09-5.00 (2H, m), 4.51 (2H, br s), 3.50 (1H, dd, J=9.0, 4.0 Hz), 3.32 (1H, dd, J=9.0, 7.5 Hz), 2.92-2.77 (1H, m), 2.23 (1H, hextet, J=7.0 Hz), 1.36 (2H, br s), 1.00 (3H, d, J=7.0 Hz); $^{13}$C NMR (CDCl$_3$, 75 MHz) δ 140.70, 138.27, 128.25, 127.52, 127.46, 115.34, 73.61, 73.16, 54.82, 41.15, 16.74; HRMS (CI) m/z calcd. for C$_{13}$H$_{20}$NO (MH$^+$) 206.1545, found 206.1550.

(ii) Compound (4b)

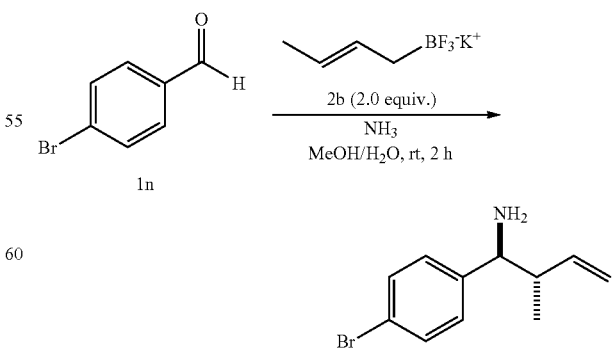

(iii) (1S*,2S*)-1-(4-Methoxyphenyl)-2-methylbut-3-en-1-amine (4c)

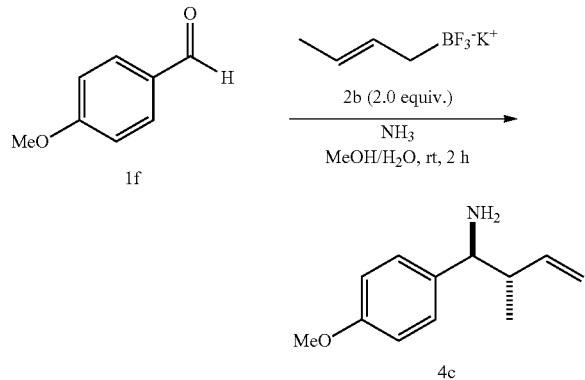

4c was isolated as a clear, colorless oil: $^1$H NMR (CDCl$_3$, 300 MHz) δ 7.20 (2H, d, J=8.5 Hz), 6.83 (2H, d, J=8.5 Hz), 5.71 (1H, ddd, J=17.5, 10.0, 8.5 Hz), 5.13 (1H, dd, J=17.5, 2.0 Hz), 5.07 (1H, dd, J=10.0, 2.0 Hz), 3.76 (3H, s), 3.56 (1H, d, J=8.0 Hz), 3.29 (1H, hextet, J=7.0 Hz), 1.48 (2H, br s), 0.78 (3H, d, J=7.0 Hz); $^{13}$C NMR (CDCl$_3$, 75 MHz) δ 158.46, 141.76, 136.54, 128.07, 115.47, 113.42, 59.86, 55.01, 46.35, 17.49; HRMS (CI) m/z calcd. for C$_{13}$H$_{20}$NO (MH$^+$) 206.1545, found 206.1550.

(iv) (1S*,2R*)-1-(1H-Indol-3-yl)-2-methylbut-3-en-1-amine (4d)

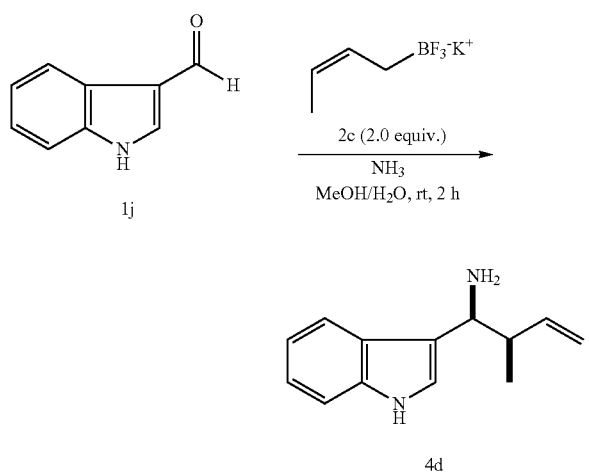

4d was isolated as a clear, colorless oil: $^1$H NMR (CDCl$_3$, 500 MHz) δ 8.82 (1H, br s), 7.71 (1H, d, J=8.0 Hz), 7.32 (1H, d, J=8.0 Hz), 7.22 (1H, t, J=7.0 Hz), 7.16 (1H, t, J=7.0 Hz), 7.04 (1H, d, J=2.0 Hz), 5.94 (1H, ddd, J=17.5, 10.5, 7.0 Hz), 5.16 (1H, dd, J=17.5, 1.5 Hz), 5.10 (1H, dd, J=10.5, 1.5 Hz), 4.37 (1H, d, J=5.0 Hz), 2.78 (1H, J=5.5 Hz), 1.68 (2H, br s), 1.07 (3H, d, J=7.0 Hz); $^{13}$C NMR (CDCl$_3$, 125 MHz) δ 158.46, 141.76, 136.54, 128.07, 115.47, 113.42, 59.86, 55.01, 46.35, 17.49.

Discussion:

The addition of potassium (E) or (Z)-crotyltrifluoroborate, (2b) or (2c) respectively, to aldehydes, when first pretreated with ammonia, has been found to lead cleanly and efficiently to the formation of the corresponding secondary carbinamines. The results are shown in Table 2. Excellent diastereoselectivities were observed with all the tested substrates, in which the (E)-crotyl reagent (2b) afforded the anti-homoallylic amine, and the (Z)-crotyl reagent (2c) afforded the syn-homoallylic amine. The resulting secondary carbinamines were easily isolated and uniformly obtained in high yields through standard acid-base extraction, and did not require any subsequent purification.

Example 3

General Procedure for the Allylation of Ketones with Potassium Allyltrifluoroborate in the Presence of Ammonia A solution of ammonia in methanol (ca. 7N in MeOH, 3.0 mL) was added to the ketone (0.5 mmol). The resulting solution was stirred for 15 minutes at room temperature, followed by the addition of potassium allyltrifluoroborate (2a) (392 mg, 1.5 mmol) and water (0.6 mL). The reaction mixture was subsequently stirred for 24 hours at room temperature. The volatiles were removed in vacuo and the residue redissolved in Et$_2$O (15 mL). Aqueous HCl (1 N, 15 mL) was then added dropwise. The biphasic mixture was vigorously shaken, and the layers were separated. The acidic aqueous layer was washed with Et$_2$O (3×15 mL), and made basic by the addition of solid NaOH (ca. 5 g). The aqueous layer was then extracted with CH$_2$Cl$_2$ (3×15 mL). The combined organic extracts were dried (Na$_2$SO$_4$), filtered and concentrated in vacuo to afford the desired tertiary carbinamine (6).

(i) 3-Methyl-1-phenylhex-5-en-3-amine (6a)

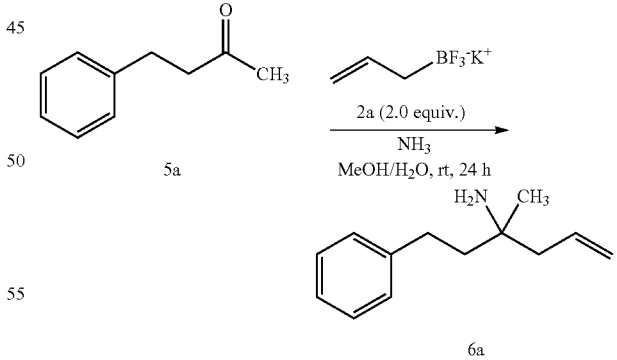

6a was isolated as a clear, colorless oil: $^1$H NMR (CDCl$_3$, 300 MHz) δ 7.32-7.23 (2H, m), 7.21-7.12 (3H, m), 5.86 (1H, ddd, J=17.0, 10.5, 7.5 Hz), 5.17-5.05 (2H, m), 2.70-2.59 (1H, m), 2.17 (1H, d, J=7.5 Hz), 1.70-1.60 (1H, m), 1.20 (2H, br s); $^{13}$C NMR (CDCl$_3$, 75 MHz) δ 142.54, 134.22, 128.20, 128.13, 125.52, 118.06, 51.27, 47.32, 44.68, 30.34, 27.69; HRMS (CI) m/z calcd. for C$_{13}$H$_{20}$N (MI-r) 190.1596, found 190.1601.

(ii) 4-Ethylhexpt-1-en-4-amine (6b)

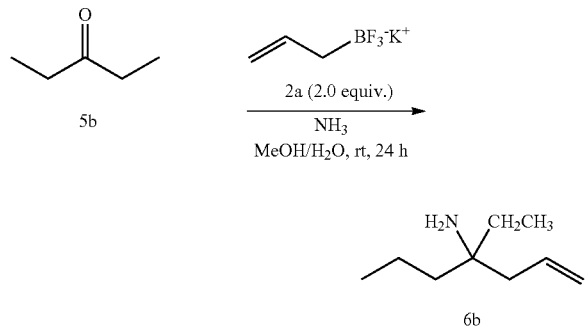

6b was isolated as a clear, colorless oil: $^1$H NMR (CDCl$_3$, 300 MHz) δ 5.77 (1H, ddt, J=16.0, 11.0, 7.5 Hz)), 5.04 (1H, d, J=11.0 Hz), 5.03 (1H, d, J=16.0 Hz), 2.03 (2H, d, J=7.5 Hz), 1.32 (4H, q, J=7.5 Hz), 1.18 (2H, br s), 0.81 (6H, t, J=7.5 Hz); $^{13}$C NMR (CDCl$_3$, 75 MHz) δ 134.44, 117.69, 53.36, 43.85, 31.66, 7.70; IR (film) u 3420, 1636 cm$^{-1}$; HRMS (ESI) m/z calcd. for C$_8$H$_{18}$N (MH$^+$) 128.1439, found 128.1444.

(iii) Compound (6c)

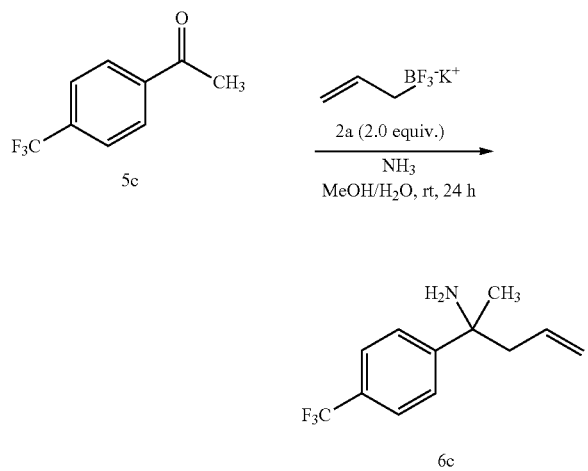

(iv) Methyl-4-(2-aminopent-4-en-2-yl)benzoate (6d)

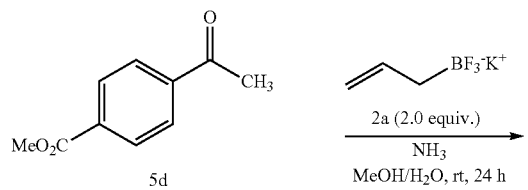

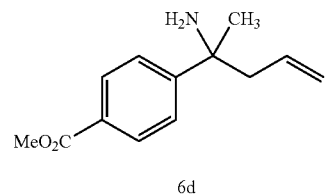

6d was isolated as a clear, colorless oil: $^1$H NMR (CDCl$_3$, 500 MHz) δ 7.99 (2H, d, J=8.5 Hz), 7.53 (2H, d, J=8.5 Hz), 5.56-5.46 (1H, m), 5.06 (1H, dd, J=17.0, 1.5 Hz), 5.05 (1H, dd, J=10.0, 1.5 Hz), 3.90 (3H, s), 2.57 (1H, dd, J=13.5, 6.5 Hz), 2.41 (1H, d, J=13.5, 8.0 Hz), 1.62 (2H, br s), 1.48 (3H, s); $^{13}$C NMR (CDCl$_3$, 125 MHz) δ 167.01, 153.92, 133.72, 129.51, 128.16, 125.40, 118.99, 54.91, 52.01, 49.60, 30.82; HRMS (CI) m/z calcd. for C$_{13}$H$_{18}$NO$_2$ (MH$^+$) 220.1338, found 220.1343.

(v) 2-(pyridin-3-yl)pent-4-en-2-amine (6e)

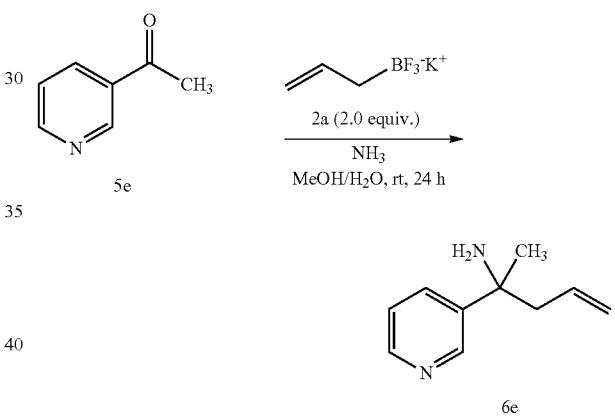

6e was isolated as a clear, colorless oil: $^1$H NMR (CDCl$_3$, 500 MHz) δ 8.69 (1H, d, J=2.0 Hz), 8.41 (1H, dd, J=5.0, 1.5 Hz), 7.75 (1H, dt, J=8.0, 2.0 Hz), 7.20 (1H, dd, J=8.0, 5.0 Hz), 5.57-5.46 (1H, m), 5.02 (1H, dd, J=10.5, 1.5 Hz), 5.01 (1H, dd, J=17.0, 1.5 Hz), 2.52 (1H, dd, J=13.5, 7.0 Hz), 2.39 (1H, dd, J=13.5, 8.0 Hz), 2.35 (2H, br s), 1.45 (3H, s); $^{13}$C NMR (CDCl$_3$, 125 MHz) δ 147.46, 147.28, 143.29, 133.18, 133.07, 122.84, 119.23, 53.65, 49.23, 30.34.

(vi) 2-(1H-pyrrol-3-yl)pent-4-en-2-amine (6f)

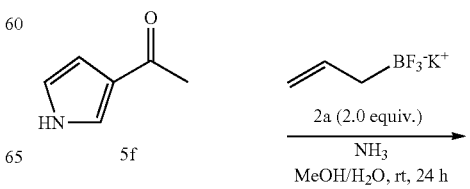

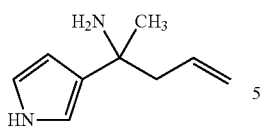

6f 6f isolated as a clear, colorless oil: $^1$H NMR (CDCl$_3$, 500 MHz) δ 8.72 (1H, br s), 6.68 (1H, dd, J=4.0, 3.0 Hz), 6.14 (1H, dd, J=6.0, 3.0 Hz), 5.97 (1H, t, J=3.0 Hz), 5.74 (1H, dddd, J=17.5, 10.5, 9.5, 7.0 Hz), 5.15-5.05 (2H, m), 2.49 (1H, dd, J=13.5, 7.0 Hz), 2.41 (1H, dd, J=13.5, 9.5 Hz), 1.73 (2H, br s), 1.44 (3H, s); $^{13}$C NMR (CDCl$_3$, 125 MHz) δ 139.13, 134.31, 118.60, 115.88, 108.21, 103.11, 51.71, 49.09, 30.68.

(vii) Compound (6g)

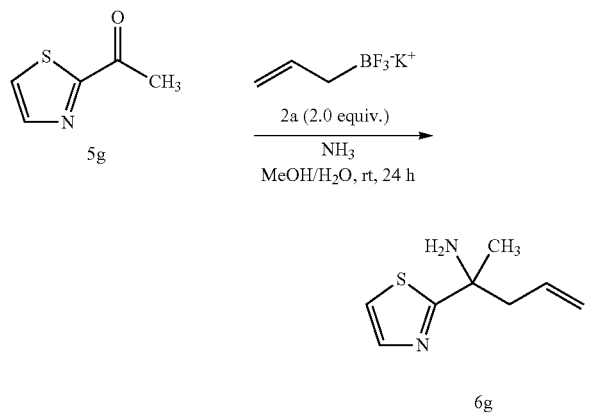

(viii) Compound (6h)

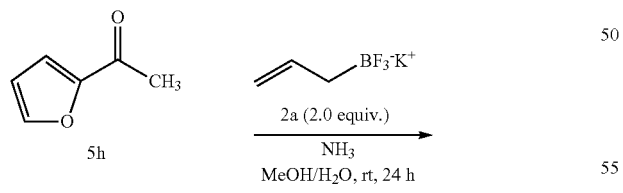

(ix) 4-Prop-2-en-1-yltetrahydro-2H-thiopyran-4-amine (6i)

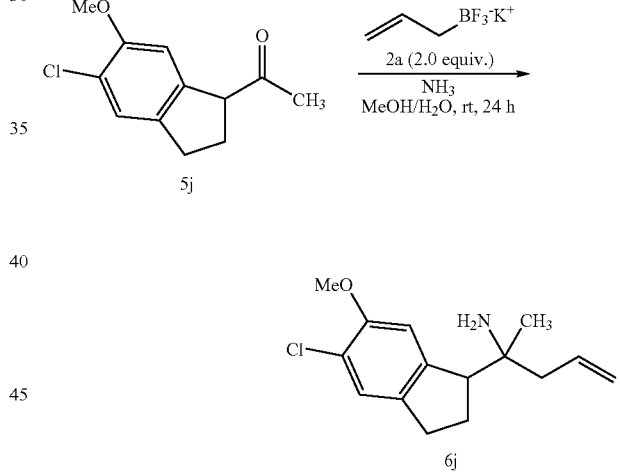

6i was isolated as a clear, colorless oil: $^1$H NMR (CDCl$_3$, 300 MHz) δ 5.72 (1H, m), 5.03 (1H, dd, J=10.0, 2.0 Hz), 4.98 (1H, dd, J=17.5, 2.0 Hz), 2.75 (2H, ddd, J=14.0, 10.0, 3.0 Hz), 2.43-2.32 (2H, m), 2.00 (2H, d, J=7.5 Hz), 1.65 (2H, ddd, J=13.5, 10.0, 3.5 Hz), 1.54 (2H, ddd, J=13.5, 6.5, 3.5 Hz), 0.97 (2H, br s); $^{13}$C NMR (CDCl$_3$, 75 MHz) δ 133.03, 118.90, 49.52, 48.09, 39.10, 24.12; HRMS (ESI) m/z calcd. for C$_8$H$_{16}$NS (MH$^+$) 158.1003, found 158.0099.

(x) Compound (6j)

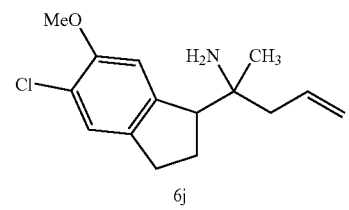

(xi) Compound (6k)

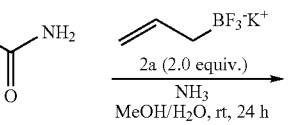

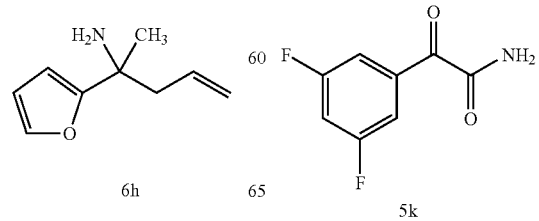

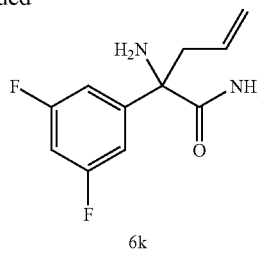

6k

(xii) 2-Methyl-2-(2-phenylethyl)pent-4-enamide (6l)

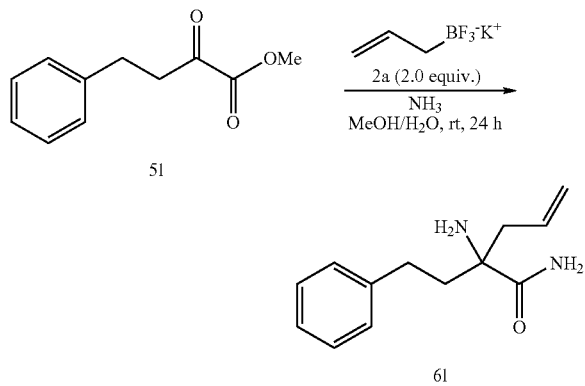

6l isolated as a clear, colorless oil: $^1$H NMR (CDCl$_3$, 300 MHz) δ 7.43 (1H, br s), 7.31-7.22 (2H, m), 7.21-7.14 (3H, m), 6.22 (1H, br s), 5.77 (1H, dddd, J=17.0, 10.0, 8.5, 6.0 Hz), 5.16 (1H, dd, J=10.0, 2.0 Hz), 5.13 (1H, dd, J=17.0, 2.0 Hz), 2.70-2.45 (3H, m), 2.25-2.10 (2H, m), 1.72 (1H, ddd, J=13.5, 11.5, 5.5 Hz), 1.50 (2H, br s); $^{13}$C NMR (CDCl$_3$, 75 MHz) δ 178.80, 141.77, 133.22, 128.50, 128.42, 126.00, 119.68, 60.26, 45.45, 42.36, 30.49.

(xiii) Compound (6m)

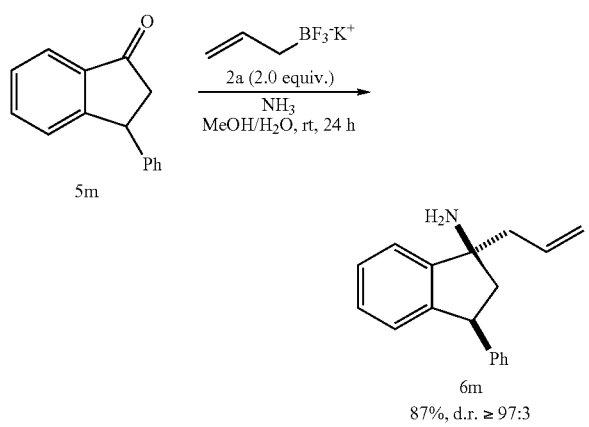

6m isolated as a clear, colorless oil: $^1$H NMR (CDCl$_3$, 300 MHz) δ 7.30-7.09 (8H, m), 6.84 (1H, d, J=7.5 Hz), 5.87-5.69 (1H, m), 5.19-5.04 (2H, m), 4.19 (1H, t, J=9.2 Hz). 2.69 (1H, dd, J=12.5, 7.5 Hz), 2.47-2.30 (2H, m), 1.93 (1H, t, J=10.5 Hz), 1.77 (2H, br s); $^{13}$C NMR (CDCl$_3$, 75 MHz) δ 149.83, 144.99, 144.20, 133.98, 128.39, 128.21, 127.42, 126.77, 126.36, 124.91, 122.51, 118.68, 62.54, 52.56, 47.98, 45.38; HRMS (ESI) m/z calcd. for C$_{18}$H$_{20}$N (MH$^+$) 250.1596, found 250.1590.

(xiv) Compound (6n)

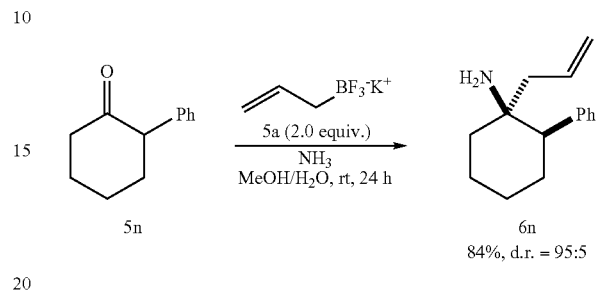

6n isolated as a clear, colorless oil: $^1$H NMR (CDCl$_3$, 300 MHz) δ 7.30-7.07 (5H, m), 5.80-5.62 (1H, m), 4.93 (1H, d, J=10.0 Hz), 4.84 (1H, d, J=17.5 Hz), 2.47 (1H, dd, J=13.0, 3.0 Hz), 2.03-1.84 (2H, m), 1.80-1.65 (2H, m), 1.60-1.42 (4H, m), 1.40-1.15 (2H, m), 1.05 (2H, br s); $^{13}$C NMR (CDCl$_3$, 75 MHz) δ 142.73, 134.19, 129.01, 127.77, 126.19, 117.79, 52.93, 52.31, 48.14, 37.61, 28.35, 26.50, 21.54; HRMS (ESI) m/z calcd. for C$_{18}$H$_{20}$N (MH$^+$) 216.1752, found 216.1759.

(xv) Compound 6o

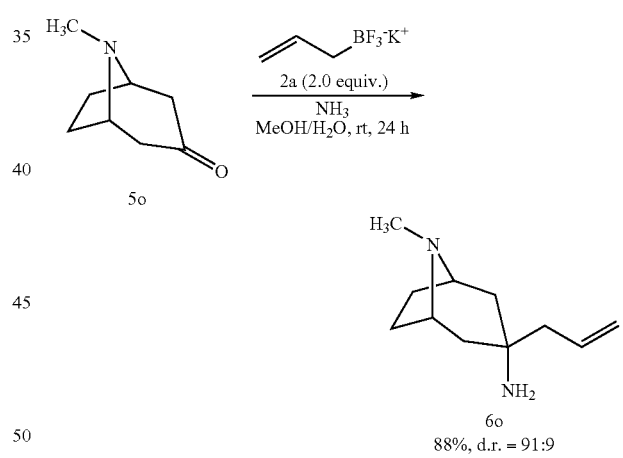

6o isolated as a clear, colorless oil: $^1$H NMR (CDCl$_3$, 300 MHz) δ 5.62 (1H, ddd, J=17.0, 10.0, 7.5 Hz), 4.96 (1H, dd, J=10.0, 2.0 Hz), 4.88 (1H, dd, J=17.0, 2.0 Hz), 3.00-2.91 (2H, m), 2.12 (3H, s), 2.00-1.67 (8H, m), 1.20 (2H, d, J=13.0 Hz), 1.01 (2H, br s); $^{13}$C NMR (CDCl$_3$, 75 MHz) δ 133.54, 118.42, 60.44, 54.19, 48.65, 47.19, 43.85, 39.88, 38.02, 27.41, 25.28.

Discussion:

The reactivity of trifluoroborates (2) was also investigated in reactions with ketones. Although ketones are generally less reactive than aldehydes, a range of ketones were successfully allylated with potassium allyl trifluoroborate 2a and the results are shown in Table 3. Aliphatic (entries 1 and 2), aromatic (entries 3 and 4), heteroaromatic (entries 5 to 8) and cyclic ketones (entries 9 and 10) are found to be useful substrates, affording the desired tertiary carbinamines (6) in good to excellent yields. Pyruvate derivatives (entries 11 and 12) are also found to be very reactive under the standard conditions. In most cases, pure products were obtained after simple acid-base extractions, and did not require any purifications by chromatography.

Still further, the present inventors have expanded the scope of the study to include the allylation of ketones containing a pre-existing stereocenter. The substrates (5m, 5n and 5o) were subjected to the standard set of reaction and work-up conditions, the results are shown in Table 4. Excellent yields of tertiary carbinamines 6m (87%), 6n (84%) and 6o (88%) were obtained in all cases. More significantly, excellent diastereoselectivities were observed with all the tested substrates, 6m (d.r.≧97:3), 6n (d.r.=95:5) and 6o (d.r.=91:9).

Example 4

General Procedure for the Crotylation of Ketones with Potassium (E) or (Z)-Crotyltrifluoroborate in the Presence of Ammonia A solution of ammonia in methanol (ca. 7N in MeOH, 3.0 mL) was added to the ketone (0.5 mmol). The resulting solution was stirred for 15 minutes at room temperature, followed by the addition of potassium crotyltrifluoroborate (2b or 2c) (392 mg, 1.5 mmol) and water (0.6 mL). The reaction mixture was subsequently stirred for 24 hours at room temperature. The volatiles were removed in vacuo and the residue redissolved in Et$_2$O (15 mL). Aqueous HCl (1N, 15 mL) was then added dropwise. The biphasic mixture was vigorously shaken, and the layers were separated. The acidic aqueous layer was washed with Et$_2$O (3×15 mL), and made basic by the addition of solid NaOH (ca. 5 g). The aqueous layer was then extracted with CH$_2$Cl$_2$ (3×15 mL). The combined organic extracts were dried with Na$_2$SO$_4$, filtered and concentrated in vacuo to afford the desired tertiary carbinamine (7).

(i) (2S*,3S*)-2-Amino-3-methyl-2-(1-methyl-1H-indol-3-yl)pent-4-enamide (7a)

7a was isolated as a clear, colorless oil: $^1$H NMR (CDCl$_3$, 300 MHz) δ 8.06 (1H, d, J=8.0 Hz), 7.45 (1H, br s), 7.32-7.25 (2H, m), 7.22 (1H, t, J=7.5 Hz), 7.16-7.10 (2H, m), 6.06 (1H, ddd, J=17.0, 10.5, 7.5 Hz), 5.27 (1H, dd, J=10.5, 2.0 Hz), 5.22 (1H, dd, J=17.0, 2.0 Hz), 3.86-3.78 (1H, m), 3.77 (3H, s), 0.95 (3H, d, J=7.0 Hz); $^{13}$C NMR (CDCl$_3$, 75 MHz) δ 177.29, 139.10, 137.49, 127.15, 125.90, 121.76, 121.68, 119.42, 117.12, 115.71, 109.43, 64.10, 41.68, 32.91, 11.99.

(ii) (2S*,3R*)-2-Amino-3-methyl-2-(1-methyl-1H-indol-3-yl)pent-4-enamide (7b)

7b was isolated as a clear, colorless oil: $^1$H NMR (CDCl$_3$, 300 MHz) δ 7.92 (1H, d, J=8.0 Hz), 7.31-7.08 (5H, m), 6.64 (1H, br s), 5.93 (1H, ddd, J=17.5, 10.5, 6.5 Hz), 5.46 (1H, br s), 5.20 (1H, dd, J=17.5, 2.0 Hz), 5.13 (1H, dd, J=10.5, 2.0 Hz), 3.75 (3H, s), 3.45 (1H, pentet, J=7.0 Hz), 1.18 (3H, d, J=7.0 Hz); $^{13}$C NMR (CDCl$_3$, 75 MHz) δ 176.17, 139.22, 137.58, 127.86, 125.82, 121.91, 121.16, 119.71, 117.11, 115.41, 109.58, 78.96, 43.70, 32.98, 13.69.

(iii) Compound (7c)

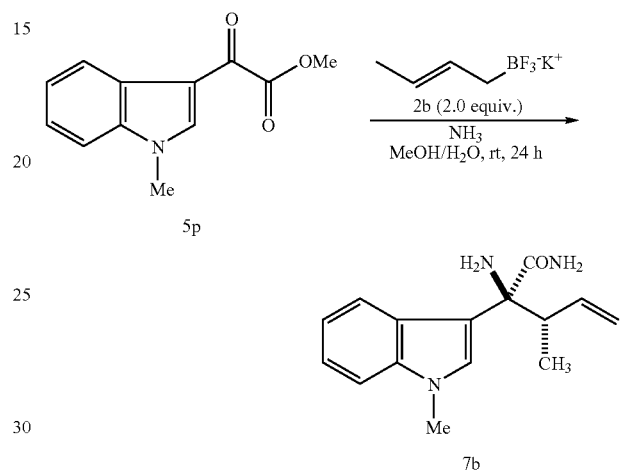

(iv) (2S*,3S*)Methyl-4-(2-amino-3-methylpent-4-en-2-yl)benzoate (7d)

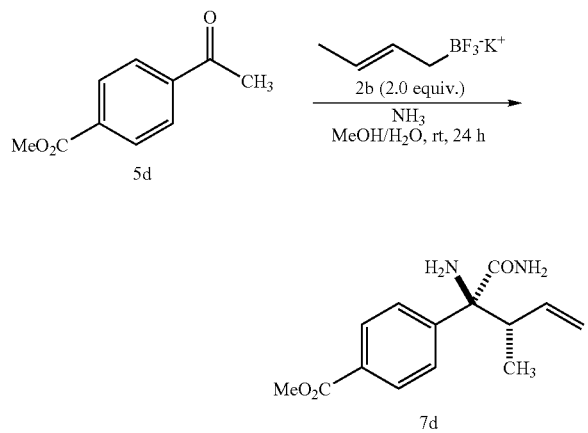

7d was isolated as a clear, colorless oil: $^1$H NMR (CDCl$_3$, 500 MHz) δ 7.98 (2H, d, J=8.5 Hz), 7.53 (2H, d, J=8.5 Hz), 5.58 (1H, ddd, J=17.5, 10.0, 7.5 Hz), 5.07-4.99 (2H, m), 3.89 (3H, s), 2.53 (1H, pentet, J=7.0 Hz), 1.55 (2H, br s), 1.43 (3H, s), 0.90 (3H, d, J=7.0 Hz); $^{13}$C NMR (CDCl$_3$, 125 MHz) δ 167.01, 153.66, 139.67, 129.19, 128.06, 125.96, 116.32, 57.11, 51.94, 48.77, 26.92, 14.27; HRMS (ESI) m/z calcd. for C$_{14}$H$_{20}$NO$_2$ (MH$^+$) 234.1494, found 234.1488.

Discussion:

The crotylation of a selected number of ketones was examined (Table 5). Excellent diastereoselectivities were obtained for all of the tested ketones. The anti diastereomers (7b, 7c and 7d) were formed when (E)-crotyltrifluoroborate (2b) was employed as the reagent, while (Z)-crotyltrifluoroborate (2c) afforded the syn diastereomer (7a).

Example 5

Addition of Organometallic Reagents to Aldehydes in the Presence of Ammonia (i) General Procedure for the Addition of Phenylmagnesium Bromide A solution of ammonia in methanol (ca. 7N in MeOH, 2.0 mL) was added to the ketone (0.5 mmol). The resulting solution was stirred for 12 hours at room temperature and all volatiles were removed in vacuo. The residue was taken up in anhydrous CH$_2$Cl$_2$ (2 mL) and cooled to −78° C. Phenylmagnesium bromide (1.0 M in THF, 1.00 mL, 1.00 mmol) was then added dropwise. The reaction mixture was then stirred for 1 h at −78° C. and then slowly allowed to warm to room temperature. The reaction mixture was quenched with the addition of sat. aq. NaHCO$_3$ (5 mL) and then diluted with CH$_2$Cl$_2$ (10 mL). The layers were separated and the aqueous layer extracted with CH$_2$Cl$_2$ (5 mL). The combined organic extracts were dried (Na$_2$SO$_4$), filtered and concentrated in vacuo to afford an orange oil. The oil was subjected to silica gel chromatography (EtOAc/hexanes/Et$_3$N) to afford the desired secondary carbinamine (8).

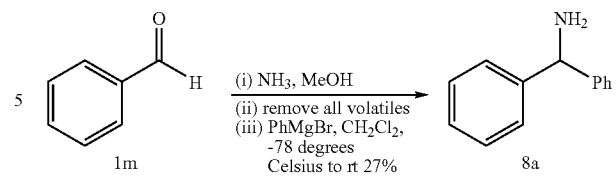

8a isolated as a clear, colorless oil. $^1$H NMR (CDCl$_3$, 300 MHz) δ 7.50-7.00 (10H, m), 5.19 (1H, s), 1.75 (2H, br s); $^{13}$C NMR (CDCl$_3$, 75 MHz) δ 145.65, 128.38, 126.87, 126.81, 59.60.

(ii) General Procedure for the Addition of Diphenyl Zinc

A solution of ammonia in methanol (ca. 7N in MeOH, 2.0 mL) was added to the ketone (0.5 mmol). The resulting solution was stirred for 12 hours at room temperature and all volatiles were removed in vacuo. The residue was taken up in anhydrous toluene (2 mL) and cooled to −78° C. Diphenylzinc (220 mg, 1.00 mmol) was then added dropwise. The reaction mixture was stirred for 1 h at −78° C. and then slowly allowed to warm to room temperature. The reaction mixture was quenched with the addition of sat. aq. NaHCO$_3$ (5 mL) and then diluted with CH$_2$Cl$_2$ (10 mL). The layers were separated and the aqueous layer extracted with CH$_2$Cl$_2$ (5 mL). The combined organic extracts were dried (Na$_2$SO$_4$), filtered and concentrated in vacuo to afford an orange oil. The oil was subjected to silica gel chromatography (EtOAc/hexanes/Et$_3$N) to afford the desired secondary carbinamine (8).

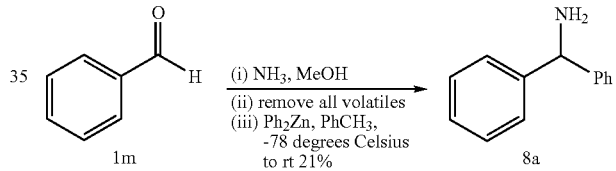

Discussion:

The scope of the study has been expanded to include the addition of an organometallic reagent to aldehydes in the presence of ammonia. Although both phenylmagnesium bromide and diphenyl zinc successfully added to benzaldehyde in the presence of ammonia, the yields of the benzylic amine obtained in both examples 9(i) and (ii) were moderate.

Example 6

Reductive Amination of Ketones and Aldehydes in the Presence of Ammonia (i) General Procedure for the Reduction of Ketones using Sodium Borohydride:

A solution ammonia in ethanol (ca. 7N in EtOH, 2.0 mL) was added to the ketone (5q) (0.5 mmol). To this solution was added sodium borohydride (38 mg, 1.00 mmol) and the reaction mixture was stirred for 16 h at room temperature. All volatiles were then removed in vacuo and the residue redissolved in CH$_2$Cl$_2$ (20 mL). The organic layer was washed with sat. aq. NaHCO$_3$ (5 mL), dried (Na$_2$SO$_4$), filtered and concentrated in vacuo to afford a yellow oil. The crude material was subjected to silica gel chromatography (EtOAc/hexanes/Et$_3$N) to afford the secondary carbinamine (8b).

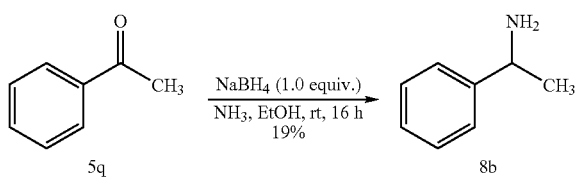

8b isolated as a clear, colorless oil. $^1$H NMR (CDCl$_3$, 300 MHz) δ 7.40-7.10 (5H, m), 4.07 (1H, q, J=7.5 Hz), 1.81 (2H, br s), 1.37 (3H, d, J=7.5 Hz); $^{13}$C NMR (CDCl$_3$, 75 MHz) δ 147.80, 128.43, 126.75, 125.71, 51.20, 25.62.

(ii) General Procedure for the Reduction of Aldehydes Using Catalytic Hydrogenation:

A solution ammonia in ethanol (ca. 7N in EtOH, 2.0 mL) was added to the aldehyde (1 1) (0.5 mmol). To this solution was added palladium on carbon (10% w/w, 186 mg, 0.05 mmol). The round bottom flask was flushed with hydrogen and then sealed with a rubber septa. The reaction mixture was then stirred for 16 h at room temperature under 1 atmosphere pressure of hydrogen (hydrogen-filled balloon). All volatiles were subsequently removed under reduced pressure. The residue was taken up in MeOH (20 mL) and filtered. The filtrate was concentrated in vacuo to afford a pale yellow oil, which was subjected to silica gel chromatography (EtOAc/hexanes/Et$_3$N) to afford the primary carbinamine (8c).

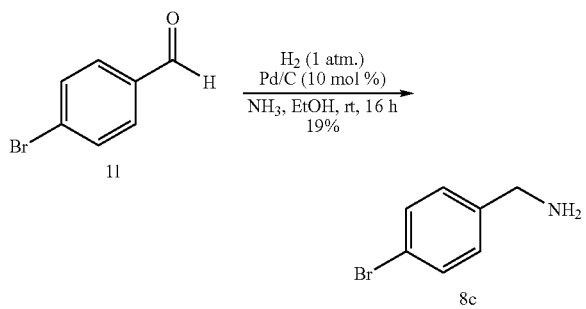

8c isolated as a clear, colorless oil. $^1$H NMR (CDCl$_3$, 300 MHz) δ 7.42 (2H, d, J=8.0 Hz), 7.22 (2H, d, J=8.0 Hz), 3.95 (2H, H), 1.70 (2H, br s).

Discussion:

Reductive amination of ketones using sodium borohydride and the reductive amination of aldehydes using catalytic hydrogenation in the presence of ethanolic ammonia has also been investigated, examples 6(i) and (ii) respectively. Both the secondary carbinamine, α-methylbenzylamine (8b), and the primary carbinamine, phenylmethanamine (8c), were obtained in moderate yields.

Example 7

General Procedure for the Resolution of Tertiary Carbinamine 6 using L-(+)-Tartaric Acid or D-(−)-Tartaric Acid L-(+)-tartaric acid or D-(−)-tartaric acid (0.150 g, 1.0 mmol) and tertiary carbinamine 6 (1.0 mmol) were suspended in CH$_2$Cl$_2$ (25 mL), and the reaction mixture was stirred at room temperature for 12 h. The resulting precipitate was filtered off and then suspended in a 5:1 mixture of CH$_2$Cl$_2$ and aqueous Na$_2$CO$_3$ (2 M) and stirred until complete dissolution occurred. The organic layer was separated off, washed with brine (10 mL), dried (MgSO$_4$) and concentrated under reduced pressure to afford 6 in an enantiomerically enriched form. The enantiomeric excess was determined by chiral HPLC.

Discussion:

Resolution of tertiary carbinamines (6) using L-(+)-tartaric acid or D-(−)-tartaric acid was investigated. The resolutions resulted in excellent enantiomeric excesses for the selected carbinamines (6) as seen in Table 6.

Example 8

General Procedure for the Enantioselective Rh-Catalyzed Addition of Potassium Allyl Trifluoroborates to Aldehydes in the Presence of Ammonia A solution of saturated ammonia in 1,4-dioxane (2 mL) was added to the aldehyde (0.5 mmol). To the resulting solution was added potassium allyl trifluoroborate (148 mg, 1.00 mmol), Rh(acac)(C$_2$H$_4$)$_2$ (6.5 mg, 0.025 mmol) and (2S,5S)-Duphos (8 mg, 0.025 mmol). Distilled and degassed water (0.4 mL) was then added and the reaction mixture heated to 80° C. in a sealed tube for 16 h. The reaction mixture was then cooled to room temperature and all volatiles removed in vacuo. The residue was redissolved in CH$_2$Cl$_2$ (20 mL) and washed with saturated aq. NaHCO$_3$ (10 mL). The organic layer was dried (Na$_2$SO$_4$), filtered and concentrated in vacuo to afford a yellow oil, which was then subjected to silica gel chromatography (EtOAc/hexanes/Et$_3$N) to afford the carbinamine (3).

(i) 1(-4-methoxyphenyl)but-3-en-1-amine

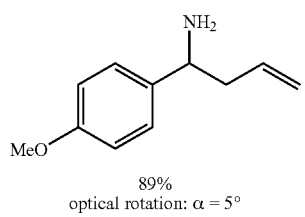

3f isolated as a clear, colorless oil: $^1$H NMR (CDCl$_3$, 300 MHz) δ 7.23 (2H, d, J=8.5 Hz), 6.84 (2H, d, J=8.5 Hz), 5.80-5.64 (1H, m), 5.13-5.00 (2H, m), 3.92 (1H, dd, J=8.0, 5.5 Hz), 3.76 (3H, s), 2.46-2.24 (2H, m), 1.48 (2H, br s); $^{13}$C NMR (CDCl$_3$, 75 MHz) δ 158.41, 137.89, 135.49, 127.18, 117.30, 113.60, 5.08, 54.65, 44.17; optical rotation: a$_D^{21}$=5°.

Discussion:

Preparation of secondary carbinamines (3) by the rhodium catalyzed addition of allyl trifluoroborates to an aldehyde was investigated using a chiral ligand (10) on the rhodium catalyst. As seen in Table 7, the rhodium catalyzed addition, with chiral ligand (10), of allyl trifluoroborates (2) to aldehydes (1) resulted in secondary carbinamines (3) in good yields with good enantioselectivies.

Example 9

General Procedure for the Rh-Catalyzed Addition of Aryl Trifluoroborate Salts to Aldehydes in the Presence of Ammonia To a solution of the aldehyde (0.5 mmol) in 1,4-dioxane saturated in ammonia (2 mL) was added the potassium aryl trifluoroborate (1.00 mmol) and Rh(acac)(C$_2$H$_4$)$_2$ (12.9 mg, 0.05 mmol). Distilled water (0.4 mL) was then added and the reaction mixture heated to 80° C. in a sealed tube for 16 h. The reaction mixture was then cooled to rt and all volatiles removed in vacuo The residue was redissolved in CH$_2$Cl$_2$ (20 mL) and washed with saturated aq. NaHCO$_3$ (10 mL). The organic layer was dried (Na$_2$SO$_4$), filtered and concentrated in vacuo to afford a yellow oil, which was then subjected to silica gel chromatography (EtOAc/hexanes/Et$_3$N). In some cases, the resulting amine was treated with HCl (1.0 M in Et$_2$O) to afford the corresponding hydrochloride salt. The salt was isolated by filtration.

(i) (4-bromophenyl)(phenyl)methanamine

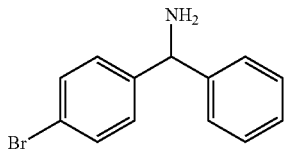

8d isolated as a clear, colourless oil. $^1$H NMR (CD$_3$OD, 300 MHz) δ 7.55 (2H, d, J=8.5 Hz), 7.50-7.13 (7H, m), 5.48 (1H, s), 1.80 (2H, br s).

(ii) phenyl(4-(trifluoromethyl)phenyl)methanamine hydrochloride salt

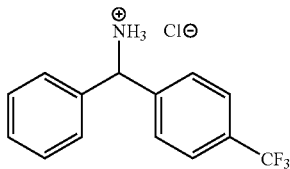

8e isolated as a white solid: mp=231-234° C.; $^1$H NMR (500 MHz, CD$_3$OD) δ 7.78 (2H, d, J=8.0 Hz), 7.64 (1H, s), 7.62 (1H, d, J=0.5 Hz), 7.51-7.41 (5H, m), 5.79 (1H, s); $^{13}$C NMR (125 MHz, CD$_3$OD) δ 143.04, 138.05 132.31 (q, J=32.0 Hz), 130.73, 130.50, 129.33, 128.78, 127.46 (q, J=4.0 Hz), 59.04.

(iii) naphthalen-2-yl(p-tolyl)methanamine hydrochloride salt

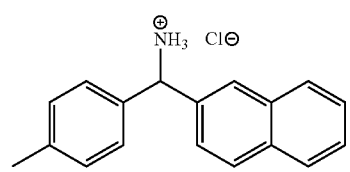

8f isolated as a white solid: mp=234-236° C.; $^1$H NMR (300 MHz, CD$_3$OD) δ 7.97-7.90 (4H, m), 7.60-7.56 (2H, m), 7.47 (1H, dd, J=9.0, 2.0 Hz), 7.38 (2H, d, J=8.5 Hz), 7.31 (2H, d, J=8.0 Hz), 5.80 (1H, s), 2.39 (3H, s); $^{13}$C NMR (75 MHz, CD$_3$OD) δ 138.90, 134.79, 134.24, 133.24, 129.52, 128.88, 127.94, 127.87, 127.46, 127.14, 126.73, 126.64, 125.86 124.38, 58.05, 19.83.

(iv) (4-chlorophenyl)(phenyl)methanamine hydrochloride salt

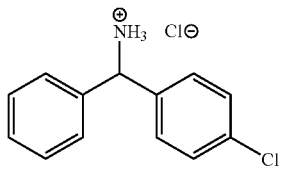

8g isolated as a white solid: m.p.=220-224° C.; $^1$H NMR (300 MHz, CD$_3$OD) δ 7.48 (9H, s), 5.71 (1H, s); $^{13}$C NMR (75 MHz, CD$_3$OD) δ 144.81, 136.92, 136.13, 134.51, 129.06, 128.97, 128.83, 128.74, 127.00, 120.26, 57.43.

Discussion:

Preparation of secondary carbinamines (8) by the rhodium catalyzed addition of aryl trifluoroborate salts to an aldehyde was investigated. As seen in Table 8, the rhodium catalyzed addition of aryl trifluoroborates (9) to aldehydes (1) resulted in secondary carbinamines (8) in good yields.

Example 10

General Procedure for the Enantioselective Rh-Catalyzed Addition of Aryl Trifluoroborate Salts to Aldehydes in the Presence of Ammonia To a solution of the aldehyde (0.5 mmol) in 1,4-dioxane saturated in ammonia (2 mL) was added the potassium aryl trifluoroborate (1.00 mmol), Rh(acac)(C$_2$H$_4$)$_2$ (6.5 mg, 0.025 mmol) and (2S,5S)-Duphos (8 mg, 0.025 mmol). Distilled and degassed water (0.4 mL) was then added and the reaction mixture heated to 80° C. in a sealed tube for 16 h. The reaction mixture was then cooled to it and all volatiles removed in vacuo. The residue was redissolved in CH$_2$Cl$_2$ (20 mL) and washed with saturated aq. NaHCO$_3$ (10 mL). The organic layer was dried (Na$_2$SO$_4$), filtered and concentrated in vacuo to afford a yellow oil, which was then subjected to silica gel chromatography (EtOAc/hexanes/Et$_3$N). The enantioselectivities were measured by chiral HPLC. In some cases, the resulting amine was treated with HCl (1.0 M in Et$_2$O) to afford the corresponding hydrochloride salt. The salt was isolated by filtration.

(i) (4-methoxyphenyl)(phenyl)methanamine

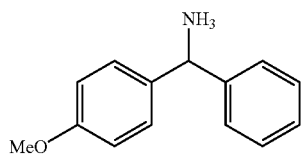

8h isolated as a clear, pale yellow oil: $^1$H NMR [300 MHz, (CD$_3$)$_2$SO]d 7.40-7.10 (7H, m), 6.85 (2H, dd, J=7.0, 2.0 Hz), 5.02 (1H, s), 3.70 (3H, s), 2.08 (2H, br s).

(ii) (4-fluorophenyl)(phenyl)methanamine hydrochloride salt

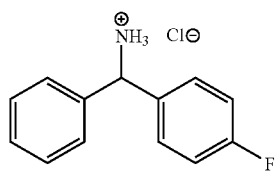

8i 8i isolated as a white solid: $^1$H NMR (400 MHz, CD$_3$OD) δ 7.50-7.42 (7H, m), 7.25-7.15 (2H, m), 5.72 (1H, s), 4.94 (3H, br s).

Discussion:

Preparation of secondary carbinamines (8) by the rhodium catalyzed addition of aryl trifluoroborates to an aldehyde was investigated using a chiral ligand (10) on the rhodium catalyst. As seen in Table 9, the rhodium catalyzed addition, with chiral ligand (10), of aryl trifluoroborates (9) to aldehydes (1) resulted in secondary carbinamines (8) in good yields with good enantioselectivies.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Addition of potassium allyltrifluoroborate (2) to aldehydes in the presence of methanolic ammonia.

| Entry | Aldehyde 1 | Yield of 3 (%)[a,b] |
|---|---|---|
| 1 | C$_7$H$_{15}$CHO | 92 (3a) |
| 2 | (CH$_3$)$_3$CCHO | 88 (3b) |
| 3 | PhCH$_2$CH$_2$CHO | 95 (3c) |
| 4 | PhCH$_2$OCH$_2$CHO | 97 (3d) |
| 5 | C$_6$H$_{11}$CHO | 90 (3e) |
| 6 | 4-MeOC$_6$H$_4$CHO | 89 (3f) |
| 7 | 3-MeOC$_6$H$_4$CHO | 99 (3g) |
| 8 | 4-NCC$_6$H$_4$CHO | 93 (3h) |
| 9 | 4-O$_2$NC$_6$H$_4$CHO | 92 (3i) |

TABLE 1-continued

Addition of potassium allyltrifluoroborate (2) to aldehydes in the presence of methanolic ammonia.

| Entry | Aldehyde 1 | Yield of 3 (%)[a,b] |
|---|---|---|
| 10 | indole-3-carboxaldehyde | 85 (3j) |
| 11 | pyridine-2-carboxaldehyde | 98 (3k) |
| 12 | furan-2-carboxaldehyde | 88 (3l) |
| 13 | thiophene-2-carboxaldehyde | 92 (3m) |

[a]Isolated yield after acid-base extraction (averaged over two runs).
[b]Analysis ($^1$H NMR, 2,4,6-trimethylbenzene standard) of the organic phase from the acid-base work-up revealed ≦5% of the corresponding homoallylic alcohol.

TABLE 2

Diastereoselective crotylation of aldehydes with potassium crotyltrifluoroborates (2b/c) in methanolic ammonia.

| Entry | Aldehyde 1 | Potassium Crotyltri-fluoroborate 2 | d.r. | Yield of 4 (%)[a] |
|---|---|---|---|---|
| 1 | PhCH$_2$OCH$_2$CHO | 2b | ≧96:4 | 89 (4a) |
| 2 | 4-BrC$_6$H$_4$CHO | 2b | ≧96:4 | 93 (4b) |
| 3 | 4-MeOC$_6$H$_4$CHO | 2b | ≧96:4 | 87 (4c) |

TABLE 2-continued

| 4 | 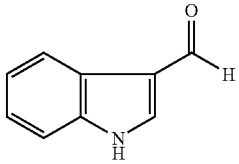 [SMILES: O=Cc1c[nH]c2ccccc12] | 2c | ≧96:4 | 88 (4d) |

[a]Isolated yield (average of two runs) after acid-base extraction.

TABLE 3

Allylation of ketones with potassium allyltrifluoroborate in methanolic ammonia.

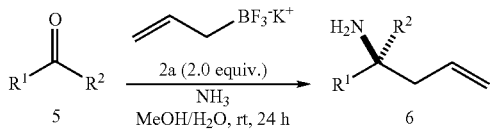

| Entry | Ketone 5 | Yield of 6 (%)[a] |
|---|---|---|
| 1 | $PhCH_2CH_2COCH_3$ | 90 (6a) |
| 2 | $Et_2C=O$ | 79 (6b) |
| 3 | $4\text{-}F_3CC_6H_4COCH_3$ | 82 (6c) |
| 4 | $4\text{-}MeO_2CC_6H_4COCH_3$ | 85 (6d) |
| 5 | 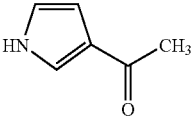 | 77 (6e) |
| 6 | 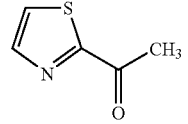 | 71 (6f) |
| 7 | 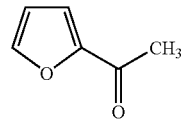 | 84 (6g) |
| 8 | 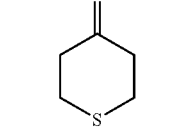 | 84 (6h) |
| 9 | 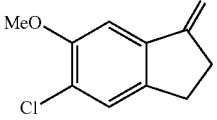 | 90 (6i) |
| 10 | 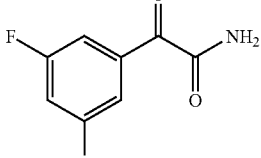 | 71 (6j) |

TABLE 3-continued

Allylation of ketones with potassium allyltrifluoroborate in methanolic ammonia.

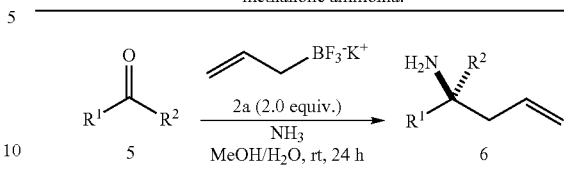

| Entry | Ketone 5 | Yield of 6 (%)[a] |
|---|---|---|
| 11 | 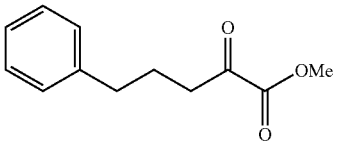 [SMILES: COC(=O)C(=O)CCCc1ccccc1] | 92 (6k) |
| 12 | 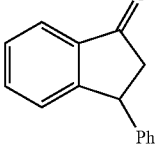 | 92 (6l) |

[a]Isolated yield (average of two runs) after acid-base extraction.

TABLE 4

Allylation of ketones with potassium allyltrifluoroborates (2a) in methanolic ammonia, in which the ketones contain a pre-existing stereocentre.

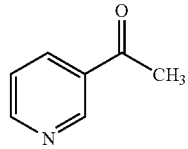

| Entry | Ketone 5 | d.r. | Yield of 6 (%)[a] |
|---|---|---|---|
| 1 | 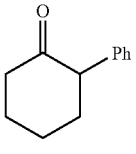 [SMILES: O=C1CCCCC1c1ccccc1] | ≧97:3 | 87 (6m) |
| 2 | 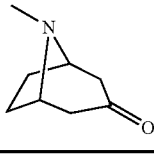 | =95:5 | 84 (6n) |
| 3 | 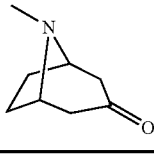 | =91:9 | 88 (6o) |

[a]Isolated yield (average of two runs) after acid-base extraction.

TABLE 5
Diastereoselective crotylation of ketones with potassium crotyltrifluoroborates (2b/c) in methanolic ammonia.
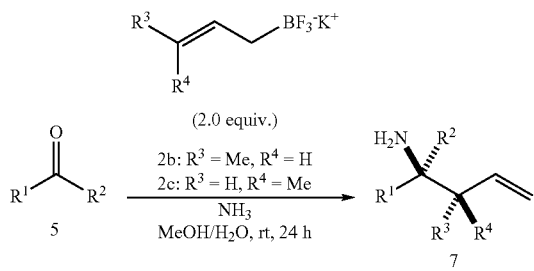
| Entry | Ketone 5 | Potassium Crotyltrifluoroborate 2 | d.r. | Yield of 7 (%)[a] |
|---|---|---|---|---|
| 1 | | 2b | ≥96:4 | 78 (7a) |
| 2 | 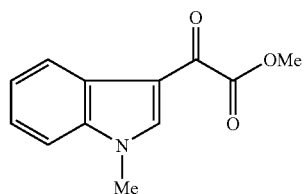 [SMILES: COC(=O)C(=O)c1cn(C)c2ccccc12] | 2c | ≥96:4 | 70 (7b) |
| 3 | 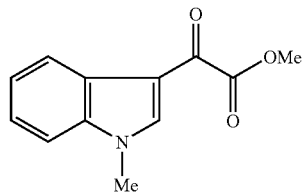 [SMILES: COC(=O)C(=O)c1cn(C)c2ccccc12] | 2b | ≥96:4 | 80 (7c) |
| 4 | 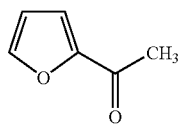 | 2b | ≥96:4 | 77 (7d) |
| | 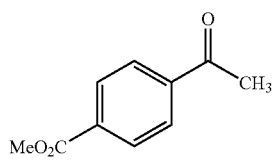 | | | |
[a]Isolated yield (average of two runs) after acid-base extraction.

TABLE 6

Resolution of Tertiary Carbinamine 6 using Tartaric Acid 6 (racemic) → 6 (enanioenriched)
Conditions: L-(+)-tartaric acid or D-(−)-tartaric acid, CH$_2$Cl$_2$, rt, 12 h

| Entry | Tertiary Carbinamine 6 | Tartaric Acid | Yield of Enantioenriched 6 | ee of 6 |
|---|---|---|---|---|
| 1 | 4-(MeO$_2$C)C$_6$H$_4$ derivative (R$^2$ = CH$_3$) | L-(+)-tartaric acid | 39 | 94 |
| 2 | 6-MeO, 5-Cl indane derivative | L-(+)-tartaric acid | 34 | 98 |
| 3 | 6-MeO, 5-Cl indane derivative | D-(−)-tartaric acid | 35 | 97 |
| 4 | PhCH$_2$CH$_2$-C(NH$_2$)(CH$_2$CH=CH$_2$)C(O)NH$_2$ | L-(+)-tartaric acid | 32 | 98 |

TABLE 7

Rhodium catalyzed enantioselective addition of potassium allyltrifluoroborate 2a to aldehydes R$^1$CHO (1) + allyl-BF$_3$K (2a) → (with (S,S)-Me-DuPhos ligand (5 mol %), Rh(acac)(C$_2$H$_4$)$_2$ (5 mol %), NH$_3$, DME/H$_2$O, 80° C., 12 h) → homoallylic amine 3

| entry | R$^1$ | yield (%) | Optical Rotation (°) |
|---|---|---|---|
| 1 | 4-MeOC$_6$H$_4$ | 89 | 5.0 |

TABLE 8

Rhodium catalyzed addition of aryl trifluoroborate salts to aldehydes in the presence of ammonia R$^1$CHO (1) + R$^2$—BF$_3$$^-$K$^+$ (9) (2.0 equiv.) → (Rh(acac)(C$_2$H$_4$)$_2$ (10 mol %), NH$_3$ (excess), Dioxane/H$_2$O, 80° C., 16 h) → R$^1$CH(NH$_2$)R$^2$ (8)

| entry | R$^1$ | R$^2$ | yield (%) |
|---|---|---|---|
| 1 | 4-BrC$_6$H$_4$ | Ph | 50 |
| 2 | Ph | 4-F$_3$CC$_6$H$_4$ | 69 |
| 3 | 4-CH$_3$C$_6$H$_4$ | 2-Naphthyl | 62 |
| 4 | Ph | 4-ClC$_6$H$_4$ | 80 |

TABLE 9

Rhodium catalyzed enantioselective addition of aryl trifluoroborate salts to aldehydes in the presence of ammonia

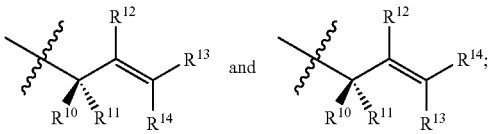

| entry | $R^1$ | $R^2$ | yield (%) | ee (%) |
|---|---|---|---|---|
| 1 | 4-MeOC$_6$H$_4$ | Ph | 62 | 62 |
| 2 | Ph | 4-FC$_6$H$_4$ | 43 | 59 |

We claim:

1. A method of preparing an amine of formula I:

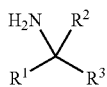

comprising reacting a compound of formula II with a compound of formula III:

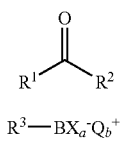

in the presence of ammonia NH$_3$ or an ammonia equivalent of the formula NH$_4^+$Y$^-$, wherein $R^1$ is H or C(O)R$^4$ in which R$^4$ is NR$^5$R$^6$ or OR$^7$, and R$^2$ is selected from C$_{1-20}$alkyl, C$_{1-20}$alkoxy, C$_{2-20}$alkenyl, C$_{2-20}$alkynyl, C$_{3-20}$cycloalkyl, C$_{3-20}$cycloalkoxy, aryl, aryloxy, heteroaryl and heteroaryloxy, all of which are optionally substituted and one or more of the carbons in C$_{1-20}$alkyl, C$_{1-20}$alkoxy, C$_{2-20}$alkynyl, C$_{3-20}$cycloalkyl or C$_{3-20}$cycloalkoxy is optionally replaced with a heteromoiety selected from O, S, N, NR$^8$ and NR$^8$R$^9$;

or $R^1$ and R$^2$ are independently selected from C$_{1-20}$alkyl, C$_{1-20}$alkoxy, C$_{2-20}$alkenyl, C$_{2-20}$alkynyl, C$_{3-20}$cycloalkyl, C$_{3-20}$cycloalkoxy, aryl, aryloxy, heteroaryl and heteroaryloxy, all of which are optionally substituted and one or more of the carbons in C$_{1-20}$alkyl, C$_{1-20}$alkoxy, C$_{2-20}$alkenyl, C$_{2-20}$alkynyl, C$_{3-20}$cycloalkyl or C$_{3-20}$cycloalkoxy is optionally replaced with a heteromoiety selected from O, S, N, NR$^8$ and NR$^8$R$^9$;

or

R$^1$ and R$^2$ are linked to form an optionally substituted monocyclic or polycyclic ring system having 4 to 20 atoms including the carbonyl to which R$^1$ and R$^2$ are bonded and one or more of the carbons of the ring system is optionally replaced with a heteromoiety selected from O, S, N, NR$^8$ and NR$^8$R$^9$;

R$^3$ is selected from aryl, heteroaryl,

R$^{10}$ to R$^{14}$ are independently selected from H, C$_{1-20}$alkyl, C$_{1-20}$alkoxy, C$_{2-20}$alkenyl, C$_{2-20}$alkynyl, C$_{3-20}$cycloalkyl, C$_{3-20}$cycloalkoxy, aryl, aryloxy, heteroaryl and heteroaryloxy, the latter 9 groups being optionally substituted and one or more of the carbons in C$_{1-20}$alkyl, C$_{1-20}$alkoxy, C$_{2-20}$alkenyl, C$_{2-20}$alkynyl, C$_{3-20}$cycloalkyl or C$_{3-20}$cycloalkoxy is optionally replaced with a heteromoiety selected from O, S, N, NR$^8$ and NR$^8$R$^9$, R$^5$, R$^6$, R$^7$, R$^8$ and R$^9$ are independently selected from H, C$_{1-20}$alkyl, C$_{3-20}$cycloalkyl, aryl and heteroaryl with the latter 4 groups being optionally substituted, X is an anionic ligand;

Y is an anionic counter ion;

Q is a cationic counter ion;

a is an integer representing the number of the anionic ligands X required to fulfill the valency requirements of B and Q; and b is an integer representing the number of the cationic counter ions Q required to fulfill the valency requirements of X and B.

2. The method according to claim 1, wherein R$^1$ in the compounds of the formulae I and II is H or C(O)R$^4$ in which R$^4$ is NR$^5$R$^6$ or OR$^1$ and R$^2$ in the compounds of the formulae I and II is selected from C$_{1-10}$alkyl, aryl and heteroaryl, all of which are optionally substituted; or R$^1$ and R$^2$ in the compounds of the formulae I and II are independently selected from C$_{1-10}$alkyl, aryl and heteroaryl, all of which are optionally substituted; or R$^1$ and R$^2$ in the compounds of the formulae I and II are linked to form an optionally substituted monocyclic or polycyclic ring system having 6 to 16 carbons including the carbonyl to which R$^1$ and R$^2$ are bonded and one or more of the carbons of the ring system is optionally replaced with a heteromoiety selected from O, S, N, NR$^8$ and NR$^8$R$^9$, in which R$^4$, R$^5$, R$^6$, R$^7$ and R$^8$ are independently selected from H, C$_{1-6}$alkyl and aryl.

3. The method according to claim 2, wherein R$^1$ in the compounds of the formulae I and II is H, C(O)NH$_2$ or C(O)OCH$_3$ and R$^2$ in the compounds of the formulae I and II is selected from methyl, ethyl, propyl, butyl, pentyl, hexyl, heptyl, phenyl, benzyl, furan, thiophene, thiazole, pyrrole, pyridyl and indole, all of which are optionally substituted.

4. The method according to claim 2, wherein R$^1$ and R$^2$ in the compounds of the formulae I and II are independently selected from methyl, ethyl, propyl, butyl, pentyl, hexyl, heptyl, phenyl, benzyl, furan, thiophene, thiazole, pyrrole, pyridyl and indole, all of which are optionally substituted.

5. The method according to claim 2, wherein R$^1$ and R$^2$ in the compounds of the formulae I and II are linked to form a ring system selected from cyclohexane, 2,3-dihydroindene, bicyclo[3.2.1]octane, bicyclo[2.2.1]heptane, bicyclo[2.2.1]octane, bicyclo[3.1.1]hept-2-ene and fluorene, all of which are optionally substituted and one or more of the carbons of cyclohexane, 2,3-dihydroindene, bicyclo[3.2.1]octane, bicyclo[2.2.1]heptane, bicyclo[2.2.1]octane, bicyclo[3.1.1]hept-2-ene and fluorene is optionally replaced with a heteromoiety selected from O, S, and $NR^8$, in which $R^8$ is H or $C_{1-6}$alkyl.

6. The method according to claim 1, wherein the optional substituents on $R^1$ and $R^2$ in the compounds of the formulae I and II are independently selected from OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-6}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

7. The method according to claim 6, wherein the optional substituents on $R^1$ and $R^2$ in the compounds of the formulae I and II are independently selected from F, Cl, Br, CN, $NO_2$, $CF_3$, $OCF_3$, $C_{1-4}$alkyl, $C_{1-4}$alkoxy, phenyl, benzyl, benzyloxy and $C(O)OC_{1-4}$alkyl.

8. The method according to claim 1, wherein $R^3$ is selected from optionally substituted aryl,

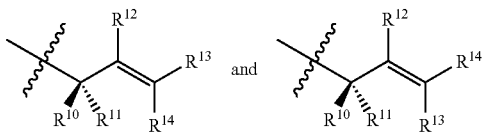

and $R^{19}$ to $R^{14}$ are independently selected from H, $C_{1-10}$alkyl, $C_{3-12}$cycloalkyl, aryl and heteroaryl, the latter 4 groups being optionally substituted, and one or more of the carbons in $C_{1-10}$alkyl or $C_{3-12}$cycloalkyl is optionally replaced with a heteromoiety selected from O, S, N, $NR^8$ and $NR^8R^9$ in which $R^8$ and $R^9$ are independently selected from H and $C_{1-6}$alkyl.

9. The method according to claim 8, wherein $R^3$ is selected from optionally substituted phenyl,

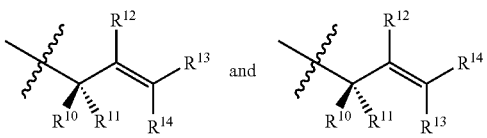

and $R^{10}$ to $R^{14}$ are independently selected from H and $C_{1-6}$alkyl.

10. The method according to claim 1, wherein the optional substituents on $R^3$ in the compounds of the formulae I and III are independently selected from OH, halo, CN, $NO_2$, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, aryl, aryloxy, aryl($C_{1-4}$alkoxy), heteroaryl, heteroaryloxy, heteroaryl($C_{1-4}$alkoxy), $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

11. The method according to claim 1, wherein X is selected from F, Cl, Br and I.

12. The method according to claim 1, wherein Q is selected from Li, Na and K.

13. The method according to claim 1, wherein X is F, Q is K, a is 3 and b is 1.

14. The method according to claim 1, wherein the method is performed in the presence of an ammonia equivalent of the formula $NH_4^+Y^-$, and wherein Y is selected from halo, $R^{16}COO$, $R^{14}SO_4$ and $BF_4$, in which $R^{16}$ is selected from $C_{1-10}$alkyl, $C_{3-20}$cycloalkyl, aryl and heteroaryl, all of which are optionally substituted; and wherein the optional substituents are independently selected from OH, halo, CN, $NO_2$, phenyl, benzyl, $C_{1-6}$alkyl, halo-substituted $C_{1-6}$alkyl, $C_{1-6}$alkoxy, halo-substituted $C_{1-6}$alkoxy, $C_{2-6}$alkenyl, $C_{2-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl and $SC_{1-4}$alkyl.

15. The method according to claim 1 wherein the method is performed in the presence of a catalyst.

16. The method according to claim 15, wherein the catalyst is a transition metal catalyst.

17. The method according to claim 16, wherein the metal is selected from rhodium, ruthenium, iridium, copper, platinum, palladium and nickel.

18. The method according to claim 17, wherein the metal is rhodium.

19. The method according to claim 15, wherein the catalyst comprises a chiral or achiral ligand.

20. The method according to claim 15, wherein the catalyst comprises a chiral ligand.

21. The method according to claim 19, wherein the ligand is a phosphine, diphosphine, aminophosphine, amine, carbene or oxazoline.

22. The method according to claim 20 wherein in the compounds of formulae I, $R^1$, $R^2$ and $R^3$ are different and enantiomerically enriched compounds of formulae I are prepared, in the compounds of formula IV, $R^1$, $R^2$ and $R^{15}$ are different and enantiomerically enriched compounds of formula IV are prepared and in the compounds of formula VI, $R^1$ and $R^2$ are different and enantiomerically enriched compounds of formula VI are prepared.

23. The method according to claim 1, wherein the method is performed at a temperature of from −40° C. to +100° C.

* * * * *

UNITED STATES PATENT AND TRADEMARK OFFICE
CERTIFICATE OF CORRECTION

PATENT NO. : 8,383,859 B2  
APPLICATION NO. : 12/593782  
DATED : February 26, 2013  
INVENTOR(S) : Avinash N. Thadani et al.

Page 1 of 1

It is certified that error appears in the above-identified patent and that said Letters Patent is hereby corrected as shown below:

In the Claims:

Column 50, line 42, replace "$OR^1$" with "$OR^7$";

Column 51, line 14, replace "$(C_{1-6}alkoxy)$" with "$(C_{1-4}alkoxy)$";

Column 51, line 33, replace "$R^{19}$" with "$R^{10}$";

Column 52, line 51, replace "-40° C." with "-40° C".

Signed and Sealed this  
Eleventh Day of June, 2013

Teresa Stanek Rea  
*Acting Director of the United States Patent and Trademark Office*